US007405342B2

(12) United States Patent
Finberg

(10) Patent No.: US 7,405,342 B2
(45) Date of Patent: Jul. 29, 2008

(54) TRANSGENIC MICE EXPRESSING HETEROLOGOUS COMPLEMENT RECEPTOR TYPE 1 (CR1) MOLECULES ON ERYTHROCYTES AND USES THEREFOR

(75) Inventor: Robert W. Finberg, Sudbury, MA (US)

(73) Assignee: University of Massachusetts, Worcester, MA (US)

( * ) Notice: Subject to any disclaimer, the term of this patent is extended or adjusted under 35 U.S.C. 154(b) by 296 days.

(21) Appl. No.: 10/843,038

(22) Filed: May 10, 2004

(65) Prior Publication Data

US 2005/0028230 A1 Feb. 3, 2005

Related U.S. Application Data

(60) Provisional application No. 60/469,262, filed on May 9, 2003.

(51) Int. Cl.
*A01K 67/027* (2006.01)
*G01N 33/00* (2006.01)
*C12N 15/00* (2006.01)

(52) U.S. Cl. .................. 800/18; 800/3; 800/8; 800/22; 800/25

(58) Field of Classification Search .............. 435/320.1; 800/3, 13–20, 8
See application file for complete search history.

(56) References Cited

U.S. PATENT DOCUMENTS

| | | | |
|---|---|---|---|
| 4,474,893 | A | 10/1984 | Reading |
| 5,212,071 | A | 5/1993 | Fearon et al. |
| 5,470,570 | A | 11/1995 | Taylor et al. |
| 5,487,890 | A | 1/1996 | Taylor et al. |
| 5,798,229 | A | 8/1998 | Strittmatter et al. |
| 5,879,679 | A | 3/1999 | Taylor et al. |
| 5,959,084 | A | 9/1999 | Ring et al. |
| 6,316,604 | B1 | 11/2001 | Fearon et al. |
| 6,479,729 | B1 | 11/2002 | Campochiaro et al. |
| 2002/0103343 | A1 | 8/2002 | Taylor et al. |

FOREIGN PATENT DOCUMENTS

| | | | |
|---|---|---|---|
| WO | WO-92/05801 | A1 | 4/1992 |
| WO | WO-95/22977 | A1 | 8/1995 |
| WO | WO-01/45669 | A1 | 6/2001 |
| WO | WO-01/80883 | A1 | 11/2001 |
| WO | WO-02/46208 | A2 | 6/2002 |
| WO | WO-02/075275 | A2 | 9/2002 |
| WO | WO-03/007971-1 | | 1/2003 |

OTHER PUBLICATIONS

Kinoshita et al. Monoclonal Antibodies to Mouse Complement Receptor Type 1 (CR1). Journal of Immunology. 1998, vol. 140, pp. 3066-3072.*

Vyas et al. Different Sequence Requirements for Expression in Erythroid and Megakaryocytic Cells within a Regulatory Element Upstream of the GATA-1 gene. Development. 1999, vol. 126, pp. 2799-2811.*

Jost et al. Intracellular Storage and Regulated Plasma Membrane Expression of Human Complement Receptor Type 1 in Rat Basophil Leukemia Cell Transfectants. Blood. 1998, vol. 92, pp. 300-309.*

McDevitt et al. An Upstream, DNase I Hypersensitive Region of the Hematopoietic-Expressed Transcription Factor GATA-1 Gene Confers Developmental Specificity in Transgenic Mice. PNAS. 1997, vol. 94, pp. 7976-7981.*

Cameron, E.R. Recent Advances in Transgenic Techology, Molec. Biotech. 1997, vol. 7, pp. 253-265.*

Sigmund, C.D. Viewpoint: Are Studies in Genetically Altered Mice Out of Control. Arteroscler. Throm. Vasc. Biol. 2000, vol. 20, pp. 1425-1429.*

Niemann, H. Transgenic Farm Animals Get Off the Ground. Transg. Res. 1998, vol. 7, pp. 73-75.*

Smith. Gene Transfer in Higher Animals: Theoretical Considerations and Key Concepts. J. Biotech. 2002, vol. 99, pp. 1-22.*

Montoliu. Gene Transfer Strategies in Animal Transgenesis. Cloning and Stem Cells. 2002, vol. 4, pp. 39-46.*

Ristevski. Making Better Transgenic Models. Molecular Biotechnology, vol. 29, pp. 153-163.*

Vik et al. Structure of the Gene for the F Allele of Complement Receptor Type 1 and Sequence of the Coding Region Unique to the S Allele. J Immunology. 1993, vol. 151, pp. 6214-6224.*

Craig, Maria L. et al., "Infusion of Bispecific Monoclonal Antibody Complexes into Monkeys Provides Immunologic Protection against Later Challenge with a Model Pathogen," *Clinical Immunology*, vol. 92(2):170-180 (1999).

Edberg, J.C. et al., "Functional characterization of non-human primate erythrocyte immune adherence receptors: implications for the uptake of immune complexes by the cells of the mononuclear phagocytic system," *Eur. J. Immunol.*, vol. 22(6):1333-1339 (1992).

Hahn, Chang S. et al., "Bispecific Monoclonal Antibodies Mediate Binding of Dengue Virus to Erythrocytes in a Monkey Model of Passive Viremia," *The Journal of Immunology*, vol. 166:1057-1065 (2001).

Klickstein, Lloyd B. et al., "Identification of Distinct C3b and C4b Recognition Sites in the Human C3b/C4b Receptor (CR1, CD35) by Deletion Mutagenesis," *J. Exp. Med.*, vol. 168:1699-1717 (1988).

Kuhn, Susan E. et al., "*Escherichia coli* Bound to the Primate Erythrocyte Complement Receptor via Bispecific Monoclonal Antibodies Are Transferred to and Phagocytosed by Human Monocytes in an In Vitro Model," *The Journal of Immunology*, vol. 160:5088-5097 (1998).

(Continued)

*Primary Examiner*—Deborah Crouch
(74) *Attorney, Agent, or Firm*—Lahive & Cockfield, LLP; Megan E. Williams

(57) ABSTRACT

The present invention is directed, at least in part, to mice which express exogenous complement receptor type 1 (CR1) on red blood cells. The invention also pertains to genetic constructs encoding heterologous CR1 for expression on red blood cells. Methods of using the transgenic animals of the invention to identify and/or evaluate compositions that can reduce the concentration of an agent, e.g., a biologic agent, in the serum, circulation and/or tissues of a subject are also provided.

24 Claims, 6 Drawing Sheets

OTHER PUBLICATIONS

Lindorfer, Margaret A. et al., "Heteropolymer-mediated clearance of immune complexes via erythrocyte CR1: mechanisms and applications," *Immunological Reviews*, vol. 183:10-24 (2001).

Little, Stephen F. et al., "Production and Characterization of Monoclonal Antibodies to the Protective Antigen Component of *Bacillus anthracis* Toxin," *Infection and Immunity*, vol. 56(7):1807-1813 (1988).

Nardin, A. et al., "A prototype pathogen bound ex vivo to human erythrocyte complement receptor 1 via bispecific monoclonal antibody complexes is cleared to the liver in a mouse model," *Eur. J. immunol.*, vol. 29(5):1581-1586 (1999).

Nardin, A. et al., "Quantitative studies of heteropolymer-mediated binding of inactivated Marburg virus to the complement receptor on primate erythrocytes," *J. Immunol. Methods*, vol. 211(1-2):21-31 (1998).

Nardin, A. et al., "How are immune complexes bound to the primate erythrocyte complement receptor transferred to acceptor phagocyte cells?" *Mol. Immunol.*, vol. 36(13-14):827-835 (1999).

Nickells, M. et al., "Mapping epitopes for 20 monoclonal antibodies to CR1," *Clin. Exp. Immunol.*, vol. 112:27-33 (1998).

Perez, P. et al., "Specific targeting of cytotoxic T cells by anti-T3 linked to anti-target cell antibody," *Nature*, vol. 316(6026):354-356 (1985).

Powers, John H. et al., "Complement-Independent Binding of Microorganisms to Primate Erythrocytes In Vitro by Cross-Linked Monoclonal Antibodies via Complement Receptor 1," *Infection and Immunity*, vol. 63(4):1329-1335 (1995).

Reilly, Brian D. et al., "Quantitative Analysis of C4b Dimer Binding to Distinct Sites on the C3b/C4b Receptor (CR1)," *The Journal of Biological Chemistry*, vol. 269(10):7696-7701 (1994).

Reist, C.J. et al., "Antigens pre-bound to the primate erythrocyte complement receptor via cross-linked bispecific monoclonal antibody heteropolymers are rapidly cleared from the circulation," *Eur. J. Immunol.*, vol. 23(11):3021-3027 (1993).

Taylor, Ronald P. et al., "Use of heteropolymeric monoclonal antibodies to attach antigens to the C3b receptor of human erythrocytes: A potential therapeutic treatment," *Proc. Natl. Acad. Sci. USA*, vol. 88:3305-3309 (1991).

Taylor, Ronald P. et al., "Clearance of blood-borne pathogens mediated through bispecific monoclonal antibodies bound to the primate erythrocyte complement receptor," *Cancer Immunol. Immunother.*, vol. 45:152-155 (1997).

Taylor, Ronald P. et al., "Bispecific Monoclonal Antibody Complexes Facilitate Erythrocyte Binding and Liver Clearance of a Prototype Particle Pathogen in a Monkey Model," *The Journal of Immunotherapy*, vol. 159:4035-4044 (1997).

Taylor, Ronald P. et al., "Bispecific Monoclonal Antibody Complexes Bound to Primate Erythrocyte Complement Receptor 1 Facilitate Virus Clearance in a Monkey Model," *The Journal of Immunology*, vol. 158:842-850 (1997).

Taylor, Ronald P. et al., "In Vivo Binding and Clearance of Circulating Antigen by Bispecific Heteropolymer-Mediated Binding to Primate Erythrocyte Complement Receptor," *The Journal of Immunology*, vol. 148(8):2462-2468 (1992).

* cited by examiner

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 1

accctttctg tcctcaca                                              18


<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 2

tttctccctc cgcttccagg ttg                                        23
```

TRANSGENIC MICE EXPRESSING HETEROLOGOUS COMPLEMENT RECEPTOR TYPE 1 (CR1) MOLECULES ON ERYTHROCYTES AND USES THEREFOR

RELATED APPLICATION

This application claims priority to U.S. provisional application Ser. No. 60/469,262 filed May 9, 2003, the contents of which are entirely incorporated by reference.

BACKGROUND OF THE INVENTION

The complement system is composed of many different proteins that are important in the immune system's response to foreign antigens. The proteins of the complement system constitute about 10% of the globulins in normal serum. The complement system becomes activated when its primary components are cleaved, and the resulting products, either alone or with other proteins, activate additional complement proteins, resulting in a proteolytic cascade. Activation of the complement system leads to a variety of responses including increased vascular permeability, chemotaxis of phagocytic cells, activation of inflammatory cells, opsonization of foreign particles, direct killing of cells and tissue damage. In the classical pathway, activation of the complement system is triggered by antigen-antibody complexes. In an alternative pathway, the complement system may be catalyzed, for example, by lipopolysaccharides present in cell walls of pathogenic bacteria.

Complement receptor type I (CR1) is a membrane glycoprotein that has been shown to be present on erythrocytes (E), monocytes/macrophages, granulocytes, B cells, some T cells, splenic follicular dendritic cells, and glomerular podocytes. CR1 mediates the binding of particles or immune complexes that contain activated complement to the surface of these cells. More specifically, CR1 binds to the complement activation products C3b and C4b, and has thus also been referred to as the C3b/C4b receptor. The consequences of these interactions depend upon the cell type bearing the receptor (Fearon, D. T. and Wong, W. W. (1983) Ann. Rev. Immunol. 1:243). CR1 on the surface of erythrocytes binds immune complexes for transport to the liver (Cornacoff, J. B. et al. (1983) J. Clin. Invest. 71:236; Nedof, N. E. et al. (1982) J. Exp. Med. 145:1739). CR1 on neutrophils and monocytes internalizes bound complexes, either by adsorptive endocytosis through coated pits or by phagocytosis after activation of the receptor by phorbol esters, chemotactic peptides or proteins that are present in the extracellular matrix, such as fibronectin and laminin (Newman S. L. et al. (1980) J. Immunol. 124:2236; Wright, S. D. and Silverstein S. C. (1982) J. Exp. Med. 145:1149; Wright S. D. et al. (1983) J. Exp. Med. 148:1338). Phosphorylation of CR1 may have a role in the acquisition of this phagocytic activity (Changelian P. S. & Fearon D. T. (1986) J. Exp. Med. 163:101). The function of CR1 on B lymphocytes is less defined, although treatment of these cells with antibody to CR1 enhanced their response to suboptimal doses of pokeweed mitogen (Daha, M. R. et al. (1983) Immunobiol. 164:227 (Abstr)). CR1 on follicular dendritic cells may serve an antigen presentation role (Klaus G. G. B. et al. (1980) Immunol. Rev. 53:3).

In addition to serving as a receptor, CR1 also has complement regulatory functions. For example, in the classical and alternative complement pathways, CR1 can inhibit the C3/C5 convertases and can also act as a cofactor for the cleavage of C3b and C4b by factor I (Fearon D. T. (1979) Proc. Natl. Acad. Sci. U.S.A. 76:5867; Liida X. & Nussenzweig V. (1981) J. Exp. Med. 153:1138). In the classical pathway of complement activation, the complex C4b, 2a is a C3 activating enzyme, or convertase. CR1 can bind to C4b and promote the dissociation of C4b,2a. This binding renders C4b susceptible to irreversible proteolytic inactivation by factor I through cleavage to the inactivated complement proteins C4c and C4d. In the alternative pathway of complement activation, the complex C3b, 4b is a C3 convertase. CR1 can bind to C3b and can also promote the dissociation of C3b, 4b. Formation of C3b, CR1 renders C3b susceptible to irreversible proteolytic inactivation by factor I, resulting in the formation of the inactivated complement protein C3b (iC3b).

CR1 is a glycoprotein composed of a single polypeptide chain. Four allotypic forms of CR1 have been found, differing in molecular weight by increments of ~40,000-50,000 daltons. The two most common forms are the F and S allotypes (also termed the A and B allotypes), having molecular weights of 250,000 and 290,000 daltons (Dykman, T. R. et al. (1983) Proc. Natl. Acad. Sci. U.S.A. 30:1698; Wong, W. W. et al. (1983) J. Clin. Invest. 72:685), respectively. There are also two rarer forms having molecular weights of 210,000 and >290,000 daltons (Dykman, T. R. et al. (1984) J. Exp. Med. 159:691; Dykman, R. R. et al. (1985) J. Immunol. 134:1787). These differences apparently represent variations in the polypeptide chain of CR1, rather than glycosylation state (Wong W. W. et al. (1983) J. Clin. Invest. 72:685). All four CR1 allotypes have C3b binding activity (Dykman, T. R. et al. (1983) Proc. Natl. Acad. Sci. U.S.A. 30:1698; Dykman, T. R. et al. (1984) J. Exp. Med. 159:691; Dykman, T. R. et al. (1985) J. Immunol. 134:1787; Wong W. W. et al (1983) J. Clin. Invest. 72:685).

While CR1 is found on various hematopoietic cells, the vast majority of CR1 in the blood is present specifically on erythrocytes. This CR1 plays a predominant role in the processing and clearance of circulating immune complexes. Once a pathogen adheres to the erythrocyte, the immune-complexed pathogen is efficiently transferred to acceptor phagocytic cells, such as fixed tissue macrophages in the liver and spleen. Interestingly, the pathogen in this transfer reaction is apparently stripped from the erythrocyte without any discernible damage to the erythrocyte (Lindorfer M. A. et al. (2001) Immun. Reviews 183:10-24). The detailed mechanism of the transfer reaction has not yet been fully elucidated. Studies suggest, however, that the in vivo transfer reaction is facilitated by a process that is unlikely to depend upon Factor I-mediated release (Lindorfer et al. (2001) Immun. Reviews 183:10-24).

An important goal in the pharmaceutical industry is the development of novel therapeutic modalities that can target and clear pathogens from tissues or the bloodstream. Several approaches undertaken to address this problem are aimed at taking advantage of the immune adherence function of primate erythrocytes. In one approach, bispecific monoclonal antibodies complexes (heteropolymers, HP) are designed to bind and immobilize a target pathogen to CR1 of a primate erythrocyte (Lindorfer M. A. et al. (2001) Immun. Reviews 183:10-24). For example, heteropolymers can consist of a monoclonal antibody specific for CR1 that is chemically cross-linked with a monoclonal antibody specific for the target pathogen. In this way, the antibody specific for CR1 serves as a surrogate for the natural CR1 ligand, C3b. One advantage of this approach is that while the natural affinity of C3b for CR1 is low, thus requiring robust complement activation and the capture of multiple C3b molecules to insure erythrocyte binding, several mouse monoclonal antibodies have been raised that possess very high affinity for CR1. Crosslinking these antibodies to a high-affinity pathogen-specific monoclonal antibody should allow for virtually any target pathogen to be bound by erythrocytes in the absence of complement. This strategy has been successfully applied to a number of bacteria and viruses (Powers J. H. et al. (1995) Infect. Immun 63:1329-1335; Kuhn S. E. et al. (1998) J. Immunol. 160:5088-5097; Nardin A., et al. (1998) 211:21-31; Hahn C. S. et al. (2001) J. Immunol 166:1057-1065).

In a related approach, the use of erythrocytes and bispecific reagents to target molecules in the serum and/or circulation can be extended to target the numerous autoantibodies associated with autoimmune diseases, such as the IgG anti-ds-DNA antibodies in systemic lupus erythematosus (SLE). The autoantibodies can be targeted for erythrocyte-mediated clearance by using antigen-based heteropolymers (AHP) (Lindorfer M. A. et al. (2001) Immun. Reviews 183:10-24). Antigen-based heteropolymers consist of an autoantigen chemically cross-linked to an anti-CR1 monoclonal antibody. The erythrocyte-bound antigen-based heteropolymer captures autoantibodies and directs the newly formed erythroycte-bound immune complex into the transfer reaction for ultimate clearance to the liver.

There is a clear need in the art for animal models that can be used to test the ability of bispecific compositions, such as heteropolymers which bind CR1, to clear targeted molecules from tissues, serum and/or the circulation. Such animal models would be useful in evaluating both the efficacy and safety of bispecific compositions and bispecific composition-based therapies. Unfortunately, while mice are an excellent model for drug testing, mice do not express CR1 on their erythrocytes (Kalli and Fearon. 1994. *J. Immunol.* 152:2894).

SUMMARY OF THE INVENTION

The present invention is based, at least in part, on the generation of mice expressing human complement receptor type 1 (CR1) and the observation that these animals express CR1 on red blood cells. Accordingly, the invention features genetic constructs and non-human animals in which a heterologous CR1 gene is expressed. Methods of using the transgenic animals of the invention to identify and/or evaluate compositions that can reduce the concentration of an agent, e.g., a biologic agent, in the tissues, serum and/or circulation of a subject are also provided.

In one aspect, the invention is directed to a genetic construct for expression in a non-human animal consisting of a nucleotide sequence encoding a human complement receptor 1 (CR1) polypeptide operably linked to a promoter, wherein the construct directs the functional expression of human CR1 on erythrocytes.

In another aspect, the invention is directed to a non-human animal whose genome includes a polynucleotide encoding human complement receptor 1 (CR1) operably linked to a promoter, wherein the human CR1 molecule is functionally expressed on the erythrocytes of the animal. Preferably, the human CR1 molecule is preferentially expressed on erythrocytes.

In preferred embodiments, the promoter is a GATA-1 promoter. More preferably, the promoter comprises the GATA-1 promoter and an upstream control region activating expression on erythrocytes.

In preferred embodiments, the non-human animal is homozygous or heterozygous for the polynucleotide. Preferably, the animal is a transgenic mouse.

In another aspect, the invention features a method for screening for a bispecific compound capable of reducing the concentration of an agent in the serum and/or circulation of a subject. This method includes the steps of: (a) administering a plurality of test compounds to a non-human animal whose genome comprises a polynucleotide encoding human complement receptor 1 (CR1) operably linked to a promoter, wherein the human CR1 is functionally expressed on erythrocytes of the non-human animal; (b) determining the ability of a bispecific compound to reduce the concentration of the agent in the serum and/or circulation of the non-human animal; and (c) selecting a bispecific compound that reduces the concentration of the agent in the serum and/or circulation of the non-human animal to thereby identify a bispecific compound capable of reducing the concentration of an agent in the serum and/or circulation of a subject.

In a related aspect, the invention provides a method for evaluating the ability of a bispecific compound to reduce the concentration of an agent in the serum and/or circulation of a subject. This method includes the steps of: (a) administering the bispecific compound to a non-human animal whose genome comprises a polynucleotide encoding human complement receptor 1 (CR1) operably linked to a promoter, wherein the human CR1 is functionally expressed on erythrocytes of the non-human animal; and (b) determining the ability of the bispecific compound to reduce the concentration of the agent in the serum and/or circulation of the non-human animal, to thereby evaluate the ability of the bispecific compound to reduce the concentration of the agent in the serum and/or circulation of a subject.

In one embodiment, these methods further include the step of administering the agent to the non-human animal. In preferred embodiments, the agent is a pathogen, a virus, a toxin, a polynucleotide, a bacterium, or an auto-antibody associated with an auto-immune disease.

In preferred embodiments, the bispecific compound binds to human CR1. Preferably, the bispecific compound is a heteropolymer or an antigen-based heteropolymer.

In preferred embodiments, the non-human animal is a transgenic mouse.

In other preferred embodiments, the promoter comprises a GATA-1 promoter or the GATA-1 promoter and an upstream control region activating expression on erythrocytes.

The invention further features a method for treating a subject that has been exposed to a biologic agent. This method includes administering a bispecific compound that is identified in methods provided by the invention to the subject, such that the subject is treated.

In a related aspect, the invention provides a method for treating a subject that is at risk of exposure to a biologic agent. This method includes administering a bispecific compound that is identified in methods provided by the invention to the subject, such that the subject is treated.

In yet another related aspect, the invention provides a method for treating a subject with an infection or auto-immune disease. This method includes administering an agent that was identified in methods provided by the invention to the subject, such that the subject is treated.

The invention further features a method for making a transgenic mouse expressing human CR1 on the surface of its erythrocytes. This method includes the steps of: a) introducing a polynucleotide encoding a human CR1 polypeptide into an egg or an embryo of a mouse, the polynucleotide operably linked to a promoter which causes human CR1 to be expressed on mouse erythrocytes; and b) allowing the egg or embryo comprising the CR1 polynucleotide to develop to term to thereby produce the transgenic mouse.

In a related aspect, the invention provides a method of producing a transgenic mouse. This method includes breeding two transgenic mice, each comprising a diploid genome comprising a polynucleotide encoding a human CR1 polypeptide, wherein the polynucleotide is expressed to produce a human CR1 polypeptide on mouse erythrocytes, to thereby produce an offspring transgenic mouse.

DETAILED DESCRIPTION OF THE INVENTION

Figure 1:
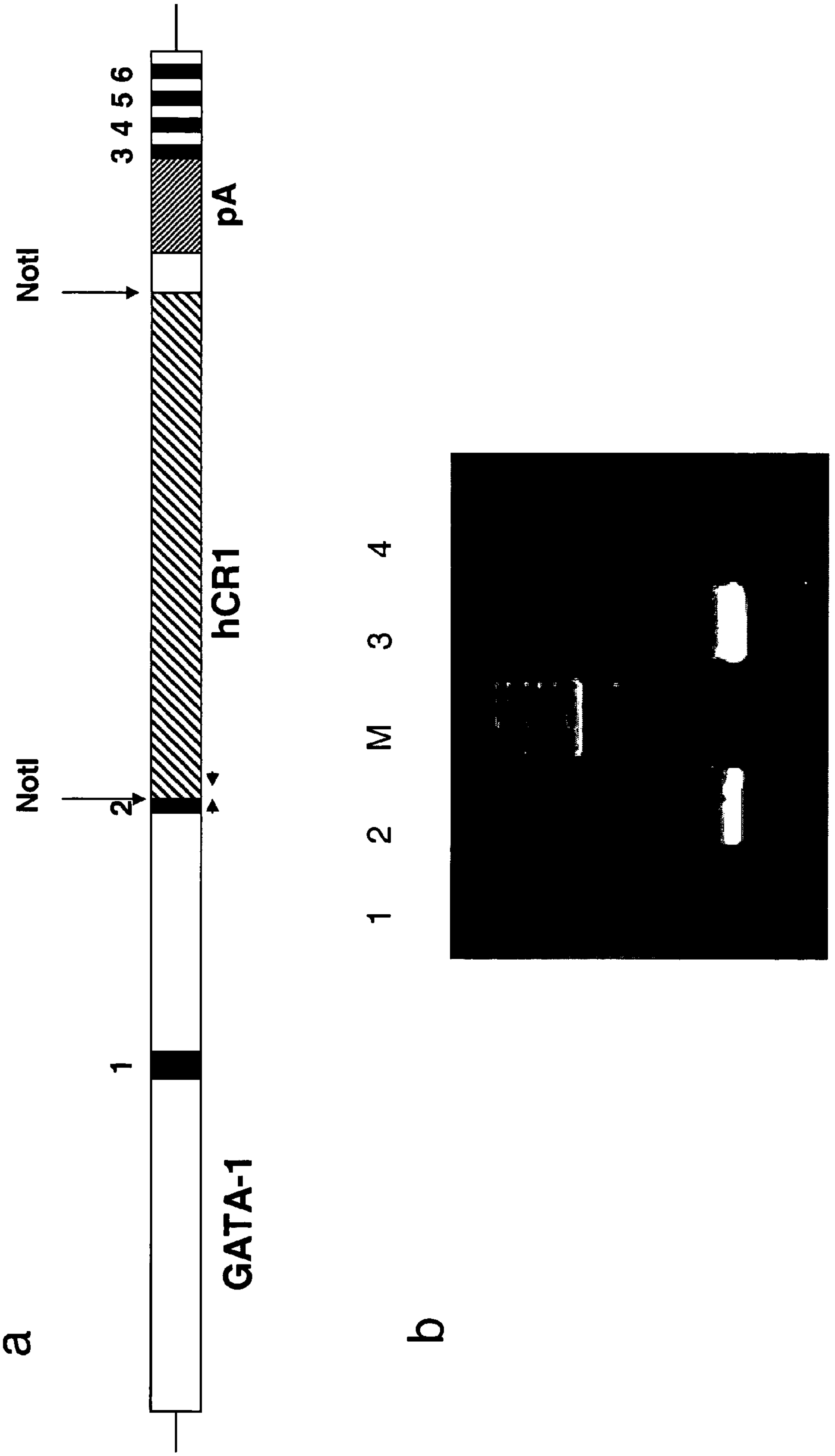
FIG. 1 displays a schematic map of the GATA1/hCR1 construct and PCR assay results that identified a transgenic founder mouse.

The present invention is based, at least in part, on the generation of mice whose genome contains a polynucleotide encoding human complement receptor 1 (CR1) operably linked to a promoter, and the observation that herologous CR1 molecules are functionally expressed on the red blood cells of the animal. Accordingly, the present invention features genetic constructs comprising CR1 and non-human animals in which CR1 is expressed on erythrocytes. The invention provides methods of using the non-human animals for identifying bispecific compounds capable of reducing the concentration of a target agent in the serum and/or circulation of a subject. The invention further features methods of treating subjects having diseases or disorders that could benefit from administration of such bispecific compounds.

So that the invention may be more readily understood, certain terms are first defined.

I. Definitions

As used herein, the term "transgene" refers to a heterologous or foreign gene or recombinant nucleic acid construct that has been incorporated into an animal. The transgene may be a wild-type or mutant gene, or one which has been altered so that it is expressed in an aberrant pattern. As used herein, the term "transgenic cell" refers to a cell containing a transgene.

As used herein the term "heterologous gene" or "foreign gene" includes genes that are not found naturally as part of the genome into which they are introduced or which are found in a location or locations in the genome that differ from that in which they occur in nature. Heterologous DNA is not endogenous to the cell into which it is introduced, but has been obtained from another cell.

As used herein, the term "genetic construct" includes non-naturally occurring nucleic acid molecules in which nucleotide sequences that are not normally present in the same molecule are engineered to be joined.

The constructs of the invention are in a form suitable for expression of the nucleic acid molecule in a host cell. Preferably, the constructs include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990).

As used herein, the term "upstream control region" includes regulatory elements that are 5' of the gene to be expressed, e.g., promoters or upstream enhancers.

As used herein, the term "promoter" includes regions of DNA involved in binding of RNA polymerase to initiate transcription.

As used herein, the term "preferentially expressed" with reference to the expression of a particular protein or a particular cell type includes expression which is greater on that cell type than on other cell types, but which is not necessarily exclusive to that particular cell type. For example, proteins that are preferentially expressed on erythrocytes are expressed at levels at least about 5-fold, at least about 10-fold, at least about 20-fold, at least about 30-fold, at least about 40-fold, at least about 50-fold or higher on erythrocytes than on other cell types.

As used herein, the term "functionally expressed" includes expression of a protein such that biological activity of the protein is maintained. For example, CR1 is functionally expressed on a cell when it is capable of binding to a natural ligand, e.g., C3b, or to an antibody.

As used herein, "transgenic animals" refers to those animals which have a heterologous or foreign gene incorporated into their genome. The term "transgenic animal" includes an animal, e.g., a non-human mammal, e.g., a swine, a monkey, a goat, or a rodent, e.g., a mouse, in which one or more, and preferably essentially all, of the cells of the animal include a transgene. The transgene is introduced into the cell, directly or indirectly by introduction into a precursor of the cell, e.g., by microinjection, transfection or infection, e.g., by infection with a recombinant virus. The term "genetic manipulation" includes the introduction of a recombinant DNA molecule. This molecule is preferably integrated within a chromosome to ensure that it will be passed on to offspring, or it may be extrachromosomally replicating DNA.

Preferred transgenic animals are mammals. According to the present invention, exemplary mammals include, without limitation, rodents (such as rats and mice), dogs, cats, pigs, sheep, cows, goats, horses and rabbits. Desirably the mammal is non-human. As used herein, the term "rodent" refers to all members of the phylogenetic order Rodentia. In a preferred embodiment, a rodent is a mouse.

As used herein, "expression" includes the synthesis of a protein by a cell. Expression of a protein can be measured at various stages, e.g., transcription, post transcription, translation, and/or post translation.

According to the present invention, transgenic animals misexpress a transgene. As used herein, the term "misexpression" includes a non-wild type pattern of gene expression. Misexpression includes: expression at non-wild type levels, i.e., a pattern of expression that differs from wild type in terms of the time or stage at which the gene is expressed, e.g., increased expression (as compared with wild type) at a predetermined developmental period or stage; a pattern of expression that differs from wild type in terms of increased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased expression (as compared with wild type) in the presence of an increase or decrease in the strength of a stimulus. Misexpression includes expression from a transgenic nucleic acid. Preferably, a transgene of the invention results in expression of the foreign gene on cells of the animal where the related endogenous gene was not previously expressed or was expressed at low levels. In one embodiment, the transgene is expressed on erythrocytes. In a preferred embodiment, the transgene is preferentially expressed on erythrocytes.

As used herein, the term "marker sequence" refers to a nucleic acid molecule that (a) is used as part of a nucleic acid targeting construct to cause the expression of the gene of interest (e.g., the CR1 gene) and (b) is used to identify those cells that have incorporated the targeting construct into their genome. For example, the marker sequence can be a sequence encoding a protein which confers a detectable trait on the cell, such as an antibiotic resistance gene, e.g., neomycin resistance gene, or an assayable enzyme not typically found in the cell, e.g., alkaline phosphatase, horseradish peroxidase, luciferase, beta-galactosidase and the like, or other conveniently detectable proteins not typically found in the cell, e.g. green fluorescent protein, red fluorescent protein.

As used herein, "administering" with respect to agents or bispecific compounds is intended to refer to dispensing, delivering or applying a composition to an animal or cell. The term "administering" is intended to refer to contacting or dispensing, delivering or applying the composition to an animal by any suitable route for delivery of the composition to the desired location in the animal, including, e.g., delivery by the parenteral or oral route, intramuscular injection, subcutaneous/intradermal injection, intravenous injection, buccal administration, transdermal delivery and administration by the intranasal or respiratory tract route.

As used herein, the term "bispecific compound" includes any bispecific compound which can potentially reduce the concentration of an agent in the serum and/or circulation of a subject. A bispecific compound is a molecule consisting of two different binding moieties. Exemplary bispecific compounds include, e.g., bispecific antibodies and heteropolymers. In preferred embodiments, the bispecific compound is a heteropolymer or an antigen-based heteropolymer.

Bispecific antibodies are single antibody molecules which have two specificities. Examples of bispecific antibodies are known in the art. Bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA*, 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Heteropolymers, as described herein, refer to molecules comprising two different binding moieties wherein at least one of the binding moieties of the heteropolymer is bivalent. For example, a heteropolymer can comprise two antibodies joined together. In one embodiment of the present invention, a heteropolymer consists of two distinct antibodies which are cross-linked by using any of a number of cross-linking techniques known in the art. In one embodiment, the heteropolymer binds human CR1. In one embodiment, a heteropolymer consists of distinct antibodies which are cross-linked by using any of a number of cross-linking techniques known in the art.

In another embodiment, a heteropolymer is an antigen-based heteropolymer. An antigen-based heteropolymer, as described herein, refers to a heteropolymer containing a binding moiety which is an antigen recognized by a target antibody, e.g. an auto-antibody associated with an autoimmune disease or disorder, wherein the binding moiety is cross-linked to a second binding moiety using any of a number of cross-linking techniques known in the art. Preferably, a second binding moiety is an antibody that binds an antigen. In one embodiment, the antigen-based heteropolymer binds to human CR1. As used herein, the term "agent" includes any substance or organism present in the serum and/or circulation of a subject that is associated with an infection, disorder or disease. Preferred agents are biologic agents include, e.g. pathogens, viruses, toxins, polynucleotides, antibodies or autoantibodies. As used herein, the term "biologic agent" also includes agents to which a subject could be exposed in biowarfare or terrorist activities, e.g. anthrax, smallpox, plague, Ebola, or Marburg virus.

The present invention is described in further detail in the following subsections.

II. CR1 Expression Constructs

In one aspect, the invention features a nucleic acid molecules which, when introduced into a non-human animal, result in functional expression of the CR1 gene on the erythrocytes of the animal. Preferably, the CR1 gene is the human CR1 gene, although other mammalian CR1 molecules can be expressed. The nucleotide sequence of the wild type human CR1 gene is known in the art and is described in, for example, Wilson J. G. et al, (1986) *J. Exp. Med.* 164:50-59, U.S. Pat. No. 6,316,604, and U.S. Pat. No. 5,212,071 the contents of which are incorporated herein by reference.

Variants of the above-referenced sequence can also be used in making the constructs of the invention. For example, different allotypes of CR1 have been described in the art. For example, such allotypes have been described by Wong et al. 1986. *J. Exp. Med.* 164:1531; Wong et al. 1989. *J. Exp. Med.* 169:847. Other human CR1 sequences are known in the art and can be found e.g., at GenBank accession No. AF169970; J. Immunol. 151: 6214(1993) or J. Biol. Chem. 265:974-980 (1990). Nucleic acid molecules encoding such allotypic forms of CR1 can also be used in the instant invention.

Variant forms of CR1, e.g., variant forms of human CR1, can also be used. The production and use of nucleic acid molecules encoding portions of a CR1 gene, modified CR1 genes, or CR1 genes which comprise a polynucleotide sequence derived from the human CR1 gene and a portion of another nucleotide sequence (e.g. CR1 sequence from another organism or a non-CR1 sequence) i.e., chimeric CR1 genes, or CR1 genes related to the human CR1 gene can also be used. Such variant forms of CR1 are capable of being functionally expressed on erythrocytes of a non-human animal and are also capable of binding to human C3b or C4b and/or to an antibody which binds to human CR1.

In one embodiment, mutations can be made to a CR1 nucleotide sequence to enhance or reduce the binding to molecules with which CR1 interacts, e.g., antibody molecules, C3b, etc.

The production and use of other nucleic acid molecules encoding a CR1 gene heterologous to the non-human animal into which they are introduced is also provided for. For example, nucleic acid sequences encoding CR1 molecules which are highly homologous to human CR1, e.g., non-human primate forms of CR1, can also be used in the instant constructs provided that such CR1 molecules or portions thereof are capable of being functionally expressed on erythrocytes of an animal and are also capable of binding to human C3b or C4b and/or to an antibody which binds to human CR1.

Variant forms of CR1 can be produced by various methods known in the art. For example, a cloned CR1 gene can be modified by any of numerous strategies known in the art (Maniatis, T., 1982, Molecular Cloning, A Laboratory Manual, Cold Spring Harbor Laboratory, Cold Spring Harbor, N.Y.). Such variants can be made, e.g., to promote or reduce binding of CR1 to CR1 binding molecules. In the production of the gene encoding a CR1 variant, preferably the modified gene will remain within the same translational reading frame as CR1, uninterrupted by translational stop signals. In another embodiment, the CR1 gene can be mutated to create and/or destroy translation, initiation, and/or termination sequences, or to create variations in coding regions and/or form new restriction endonuclease sites or destroy preexisting ones, to facilitate further in vitro modification. Known techniques for mutagenesis known in the art can be used, including but not limited to, in vitro site-directed mutagenesis (Hutchinson, C., et al., 1978, J. Biol. Chem. 253:6551), use of TAB.RTM. linkers (Pharmacia), etc. In a preferred embodiment, changes to a nucleotide sequence encoding CR1 comprise conservative mutations to the sequence.

In making the genetic constructs of the invention, an endogenous or exogenous promoter can be used. Preferably the CR1 gene is operably linked to a regulatory element (e.g., a transcriptional control element such as a promoter and/or an enhancer) which leads to expression or increased expression of CR1 on erythrocytes. The expression of CR1 need not be exclusively in erythrocytes. For example, promoters and/or enhancers that result in increased levels of expression in erythrocytes as compared to other cells may be used, even though expression on cells other than erythrocytes may result.

Suitable promoters for use in the present invention include, but are not limited to, the regulatory sequences of the GATA-1 gene. In one embodiment, the regulatory element includes an upstream control locus that is identified by DNase I hypersensitivity and which confers the activation of expression in primitive erythroid cells (see, e.g., McDevitt, M. A. et al., (1997) *Proc. Natl. Acad. Sci., USA*, 94:7976-7981; Visvader J. E. et al., (1998) *Genes & Dev.* 12(4):473-479).

Other regulatory elements are also known in the art, and include e.g., globin (see, e.g., Ristaldi et al. 1999. *Proc Natl Acad Sci USA*. 96:9654; Ristaldi et al. 1999 Blood Cells Mol. Dis. 25:193; Tewari et al. 1996. *Development*. 122:3991) β spectrin (see, e.g., Sabatino et al. 1998 *Mol Cell Biol*. 18:6634; Gallagher et al. 1999 J. Biol. Chem. 274:6062), and band 3 (see e.g., Cox et al. 1985. J. Cell Biol. 100: 1548). Regulatory sequences that control expression of other genes which are preferentially expressed in hematopoietic cells, and preferentially erythrocytes, may also be used in the invention.

Other suitable promoters can be identified, for example, by first carrying out differential expression analysis, e.g., using DNA microarray technology, to identify genes that are preferentially expressed in erythrocytes, and then identifying the corresponding regulatory sequences. For example, genes which are identified as being expressed preferentially, e.g. about 2-fold more, 5-fold more, or 10-fold more, in erythrocytes as compared to another reference cell or tissue, such as liver or heart, could be selected and their promoters identified and used in the present invention. Methods of performing differential expression analysis and DNA microarray technologies are known in the art.

An exemplary genetic construct comprises the human CR1 gene under the transcriptional control of the GATA-1 promoter and is shown in FIG. 1. Other elements which can be used to express CR1 in hematopoietic cells are known in the art and can be found, e.g., in Okuno et al. 2002. *Blood*. 100:4420; Radomska et al. 2002. *Blood*. 100:4410; Gaines et al. 2000. *J Biol Chem*. 275:34114; and Wilcox et al. 1999. *Proc Natl Acad Sci U S A*. 96:9654. Preferably, regulatory elements which more specifically increase CR1 expression on erythroid cells are employed in the instant constructs.

In one embodiment, a construct of the invention can comprise a marker gene, e.g., green fluorescent protein or an antibiotic resistance gene. Such a marker gene can be used to aid in identifying cells that express the construct.

III. Construction of Transgenic Animals

In one aspect, the present invention provides a non-human animal whose genome contains a polynucleotide encoding human complement receptor 1 (CR1) operably linked to a promoter such that the human CR1 is functionally expressed on the erythrocytes of the animal. The present invention further provides methods for making a transgenic non-human animal expressing human CR1 on the erythrocytes of the animal.

The transgenic animal used in the methods of the invention can be, e.g., a mammal, a bird, a reptile or an amphibian. Suitable mammals for uses described herein include: rodents; ruminants; ungulates; domesticated mammals; and dairy animals. Preferred animals include: rodents, goats, sheep, camels, cows, pigs, horses, oxen, llamas, chickens, geese, and turkeys. In a preferred embodiment, the non-human animal is a mouse.

Various methods of making transgenic animals are known in the art (see, e.g., Watson, J. D., et al., "The Introduction of Foreign Genes Into Mice," in Recombinant DNA, 2d Ed., W. H. Freeman & Co., New York (1992), pp. 255-272; Gordon, J. W., Intl. Rev. Cytol. 115:171-229 (1989); Jaenisch, R., Science 240: 1468-1474 (1989); Rossant, J., Neuron 2: 323-334 (1990)). An exemplary protocol for the production of a transgenic pig can be found in White and Yannoutsos, *Current Topics in Complement Research*: *64th Forum in Immunology*, pp. 88-94; U.S. Pat. No. 5,523,226; U.S. Pat. No. 5,573,933; PCT Application WO93/25071; and PCT Application WO95/04744. An exemplary protocol for the production of a transgenic rat can be found in Bader and Ganten, *Clinical and Experimental Pharmacology and Physiology*, Supp. 3:S81-S87, 1996. An exemplary protocol for the production of a transgenic cow can be found in *Transgenic Animal Technology, A Handbook*, 1994, ed., Carl A. Pinkert, Academic Press, Inc. An exemplary protocol for the production of a transgenic sheep can be found in *Transgenic Animal Technology, A Handbook*, 1994, ed., Carl A. Pinkert, Academic Press, Inc. Several exemplary methods are set forth in more detail below.

A. Injection into the Pronucleus

Transgenic animals can be produced by introducing a nucleic acid construct according to the present invention into egg cells. The resulting egg cells are implanted into the uterus of a female for normal fetal development, and animals which develop and which carry the transgene are then backcrossed to create heterozygotes for the transgene. Embryonal target cells at various developmental stages are used to introduce the transgenes of the invention. Different methods are used depending on the stage of development of the embryonal target cell(s). Exemplary methods for introducing transgenes include, but are not limited to, microinjection of fertilized ovum or zygotes (Brinster, et al., Proc. Natl. Acad. Sci. USA (1985) 82: 4438-4442), and viral integration (Jaenisch R., Proc. Natl. Acad. Sci. USA (1976) 73: 1260-1264; Jahner, et al., Proc. Natl. Acad. Sci.USA (1985) 82: 6927-6931; Van der Putten, et al., (1985) Proc. Natl. Acad. Sci. (USA) 82: 6148-6152). Procedures for embryo manipulation and microinjection are described in, for example, *Manipulating the Mouse Embryo* (Cold Spring Harbor Laboratory Press, Cold Spring Harbor, NY., 1986, the contents of which are incorporated herein by reference). Similar methods are used for production of other transgenic animals.

In an exemplary embodiment, production of transgenic mice employs the following steps. Male and female mice, from a defined inbred genetic background, are mated. The mated female mice are previously treated with pregnant mare serum, PMS, to induce follicular growth and human chorionic gonadotropin, hCG, to induce ovulation. Following mating, the female is sacrificed and the fertilized eggs are removed from her uterine tubes. At this time, the pronuclei have not yet fused and it is possible to visualize them using light microscopy. In an alternative protocol, embryos can be harvested at varying developmental stages, e.g. blastocysts can be harvested. Embryos are recovered in a Dulbecco's modified phosphate buffered saline (DPBS) and maintained in Dulbecco's modified essential medium (DMEM) supplemented with 10% fetal bovine serum.

Foreign DNA or the recombinant construct (e.g. hCR1 expression construct) is then microinjected (100-1000 molecules per egg) into a pronucleus. Microinjection of an expression construct can be performed using standard micro manipulators attached to a microscope. For instance, embryos are typically held in 100 microliter drops of DPBS under oil while being microinjected. DNA solution is microinjected into the male pronucleus. Successful injection is monitored by swelling of the pronucleus. Shortly thereafter, fusion of the pronuclei (a female pronucleus and a male pronucleus) occurs and, in some cases, foreign DNA inserts into (usually) one chromosome of the fertilized egg or zygote. Recombinant ES cells, which are prepared as set forth below, can be injected into blastocysts using similar techniques.

B. Embryonic Stem Cells

In another method of making transgenic mice, recombinant DNA molecules of the invention can be introduced into mouse embryonic stem (ES) cells. Resulting recombinant ES cells are then microinjected into mouse blastocysts using techniques similar to those set forth in the previous subsection.

ES cells are obtained from pre-implantation embryos and cultured in vitro (Evans, M J., et al., Nature 292: 154156 (1981); Bradley, M. O. et al., Nature 309: 255-258 (1984); Gossler, et al., Proc. Natl. Acad. Sci. (USA) 83:9065-9069 (1986); Robertson et al., Nature 322: 445448 (1986)). Any ES cell line that is capable of integrating into and becoming part of the germ line of a developing embryo, so as to create germ line transmission of the targeting construct, is suitable for use herein. For example, a mouse strain that can be used for production of ES cells is the 129J strain. A preferred ES cell line is murine cell line D3 (American Type Culture Collection catalog no. CRL 1934). The ES cells can be cultured and prepared for DNA insertion using methods known in the art and described in Robertson, *Teratocarcinomas and Embryonic Stem Cells: A Practical Approach*, E. J. Robertson, ed. IRL Press, Washington, D.C., 1987, in Bradley et al., *Current Topics in Devel. Biol*., 20:357-371, 1986 and in Hogan et al., *Manipulating the Mouse Embryo: A Laboratory Manual*, Cold Spring Harbor Laboratory Press, Cold Spring Harbor, NY, 1986, the contents of which are incorporated herein by reference.

The expression construct can be introduced into the ES cells by methods known in the art, e.g., those described in Sambrook et al., *Molecular Cloning: A Laboratory Manual*, $2^{nd}$ Ed., ed., Cold Spring Harbor laboratory Press: 1989, the contents of which are incorporated herein by reference. Suitable methods include, but are not limited to, electroporation, microinjection, and calcium phosphate treatment methods. The expression construct (e.g. hCR1) to be introduced into the ES cell is preferably linear. Linearization can be accomplished by digesting the DNA with a suitable restriction endonuclease selected to cut only within the vector sequence and not within the gene (e.g. hCR1 gene) or regulatory sequence (e.g. GATA-1 regulatory sequence).

After introduction of the expression construct, the ES cells are screened for the presence of the construct. The cells can be screened using a variety of methods. Where a marker gene is employed in the construct, the cells of the animal can be tested for the presence of the marker gene. For example, where the marker gene is an antibiotic resistance gene, the cells can be cultured in the presence of an otherwise lethal concentration of antibiotic (e.g. G418 to select for neo). Those cells that survive have presumably integrated the transgene construct. If the marker gene is a gene that encodes an enzyme whose activity can be detected (e.g., β-galactosidase), the enzyme substrate can be added to the cells under suitable conditions, and the enzymatic activity can be analyzed. Alternatively, or additionally, ES cell genomic DNA can be examined directly. For example, the DNA can be extracted from the ES cells using standard methods and the DNA can then be probed on a Southern blot with a probe or probes designed to hybridize specifically to the transgene. The genomic DNA can also be amplified by PCR with probes specifically designed to amplify DNA fragments of a particular size and sequence of the transgene such that, only those cells containing the targeting construct will generate DNA fragments of the proper size.

C. Implantation

The zygote harboring a recombinant nucleic acid molecule of the invention (e.g. hCR1) is implanted into a pseudo-pregnant female mouse that was obtained by previous mating with a vasectomized male. In a general protocol, recipient females are anesthetized, paralumbar incisions are made to expose the oviducts, and the embryos are transformed into the ampullary region of the oviducts. The body wall is sutured and the skin closed with wound clips. The embryo develops for the full gestation period, and the surrogate mother delivers the potentially transgenic mice. Finally, the newborn mice are tested for the presence of the foreign or recombinant DNA. Of the eggs injected, on average 10% develop properly and produce mice. Of the mice born, on average one in four (25%) are transgenic for an overall efficiency of 2.5%. Once these mice are bred they transmit the foreign gene in a normal (Mendelian) fashion linked to a mouse chromosome.

D. Screening for the Presence of the Transgenic Construct

Transgenic animals can be identified after birth by standard protocols. DNA from tail tissue can be screened for the presence of the transgene construct, e.g., using southern blots and/or PCR. Offspring that appear to be mosaics are then crossed to each other if they are believed to carry the transgene in order to generate homozygous animals. If it is unclear whether the offspring will have germ line transmission, they can be crossed with a parental or other strain and the offspring screened for heterozygosity. The heterozygotes are identified by southern blots and/or PCR amplification of the DNA. The heterozygotes can then be crossed with each other to generate homozygous transgenic offspring. Homozygotes may be identified by southern blotting of equivalent amounts of genomic DNA from mice that are the product of this cross, as well as mice that are known heterozygotes and wild type mice. Probes to screen the southern blots can be designed based on the sequence of the human CR1 gene, or the marker gene, or both.

Other means of identifying and characterizing the transgenic offspring are known in the art. For example, western blots can be used to assess the level of expression of the gene introduced in various tissues of these offspring by probing the western blot with an antibody against the protein encoded by the gene introduced (e.g., the human CR1 protein), or an antibody against the marker gene product, where this gene is expressed.

In situ analysis, such as fixing the cells and labeling with an antibody, and/or FACS (fluorescence activated cell sorting) analysis of various cells, e.g. erythrocytes, from the offspring can be performed using suitable antibodies to look for the presence or absence of the transgene product. For example, to verify expression of hCR1 on erythrocytes, flow cytometry can be performed using antibodies specific for human CR1 (e.g. 1B4, HB8592 and 7G9 monoclonals, see U.S. patent application No. 20020103343) that are directly conjugated or used in conjunction with a secondary antibody that is fluorophore-conjugated and recognizes the antibody for hCR1. In this analysis, human erythrocytes can be used as a positive control and normal mouse erythrocytes can be used as a negative control for the presence of hCR1.

E. Mice Containing Multiple Transgenes or an Additional Mutation

Transgenic mice expressing hCR1 on their circulating erythrocytes as described herein can be crossed with mice that a) harbor additional transgene(s), or b) contain mutations in other genes. Mice that are heterozygous or homozygous for each of the mutations can be generated and maintained using standard crossbreeding procedures. Examples of mice that can be bred with mice containing a hCR1 transgene include, but are not limited to, mouse strains which are more prone to an auto-immune disease, such as mouse strains which are models for Lupus, e.g. mouse strains NZB/W, MRL+ or SJL.

The invention further pertains to cells derived from transgenic animals. Because certain modifications may occur in succeeding generations due to either mutation or environmental influences, such progeny may not, in fact, be identical to the parent cell, but are still included within the scope of the term as used herein.

IV. Bispecific Compounds

In one aspect, the invention provides a method for identifying candidate or test bispecific compounds which reduce the concentration of an agent in the serum and/or circulation of a non-human animal. Compounds selected or optimized using the instant methods can be used to treat subjects that would benefit from administration of such a compound, e.g., human subjects.

Candidate compounds that can be tested in the methods of the present invention are bispecific compounds. As used herein, the term "bispecific compound" includes compounds having two different binding specificities. Exemplary bispecific compounds include, e.g., bispecific antibodies, heteropolymers, and antigen-based heteropolymers.

Bispecific molecules that can be tested in the present invention preferably include a binding moiety that is specific for CR1, preferably human CR1, crosslinked to a second binding moiety specific for a targeted agent (e.g. a distinct antibody or an antigen). Examples of binding moieties specific for CR1 include, but are not limited to, CR1 ligands, e.g. C3b or, in preferred embodiments, antibodies to CR1. Examples of monoclonal antibodies specific for CR1 include, but are not limited to, any one of the following: 1B4, HB8592, 7G9, 3D9, E-11, 57F and YZ1. HB8592 and 1B4 are disclosed in Taylor et al., *Proc. Nat. Acad. Sci.*, 88:3305-3309 (1991) and Reist et al., *Eur. J. Immunol.*, 23:3021-3027 (1993). Antibodies 3D9 and E-11 are described in Edberg et al., (1992) *Eur J Immunol.* 22: 1333-9.

In another embodiment, novel CR1 binding molecules can be identified based on their ability to bind to CR1. For example, libraries of compounds or small molecules can be tested cell-free binding assay. Any number of test compounds, e.g., peptidomimetics, small molecules or other drugs can be used for testing and can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In many drug screening programs which test libraries of modulating agents and natural extracts, high throughput assays are desirable in order to maximize the number of modulating agents surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test modulating agent. Moreover, the effects of cellular toxicity and/or bioavailability of the test modulating agent can be generally ignored in the in vitro system, the assay instead being focused primarily on the effect of the drug on the molecular target as may be manifest in an alteration of binding affinity with upstream or downstream elements.

In another embodiment, phage display techniques known in the art can be used to identify novel CR1 binding molecules.

In one embodiment, the invention provides assays for screening candidate or test compounds which bind to CR1 or biologically active portion thereof.

Cell-based assays for identifying molecules that bind to CR1 can be used to identify additional agents for use in bispecific compounds of the invention. For example, cells expressing CR1 can be used in a screening assay. For example, compounds which produce a statistically significant change in binding to CR1 can be identified.

In one embodiment of the invention CR1 or portions thereof can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with proteins of the invention and are involved in their activity. The two-hybrid system is based on the modular nature of most transcription factors, which consist of separable DNA-binding and activation domains. Briefly, the assay utilizes two different DNA constructs. In one construct, the gene that codes for an protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with a protein of the invention. Once interacting proteins have been identified, the ability of a test compound to modulate the interaction between a protein of the invention and the interacting protein can be tested using techniques that are known in the art, e.g., using the cell-free assays described herein.

In one embodiment, the assay is a cell-free assay in which a CR1 binding molecule is identified based on its ability to bind to CR1 in vitro. The CR1 binding molecule can be provided and the ability of the protein to bind CR1 can be tested using art recognized methods for determining direct binding. Determining the ability of the protein to bind to a target molecule can be accomplished, e.g., using a technology such as real-time Biomolecular Interaction Analysis (BIA). Sjolander, S. and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

The cell-free assays of the present invention are amenable to use of both soluble and/or membrane-bound forms of proteins. In the case of cell-free assays in which a membrane-bound form a protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Suitable assays are known in the art that allow for the detection of protein-protein interactions (e.g., immunoprecipitations, two-hybrid assays and the like). By performing such assays in the presence and absence of test compounds, these assays can be used to identify compounds that modulate (e.g., inhibit or enhance) the interaction of a protein of the invention with a target molecule(s).

Determining the ability of the protein to bind to or interact with a target molecule can be accomplished, e.g., by direct binding. In a direct binding assay, the protein could be coupled with a radioisotope or enzymatic label such that binding of the protein to a target molecule can be determined by detecting the labeled protein in a complex. For example, proteins can be labeled with $^{125}I$, $^{35}S$, $^{14}C$, or $^{3}H$, either directly or indirectly, and the radioisotope detected by direct counting of radioemmission or by scintillation counting. Alternatively, molecules can be enzymatically labeled with, for example, horseradish peroxidase, alkaline phosphatase, or luciferase, and the enzymatic label detected by determination of conversion of an appropriate substrate to product.

Typically, it will be desirable to immobilize either a protein of the invention or its binding protein to facilitate separation of complexes from uncomplexed forms of one or both of the proteins, as well as to accommodate automation of the assay. Binding to an upstream or downstream binding element, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/CR1 (GST/CR1) fusion proteins can be adsorbed onto glutathione sepharose beads (Sigma Chemical, St. Louis, Mo.) or glutathione derivatized microtitre plates, which are then combined with the cell lysates, e.g. an $^{35}S$-labeled, and the test modulating agent, and the mixture incubated under conditions conducive to complex formation, e.g., at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of CR1-binding protein found in the bead fraction quantitated from the gel using standard electrophoretic techniques.

Other techniques for immobilizing proteins on matrices are also available for use in the subject assay. For instance, biotinylated molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical).

It is also within the scope of this invention to determine the ability of a compound to modulate the interaction between CR1 a CR1 binding molecule, without the labeling of any of the interactants. For example, a microphysiometer can be used to detect the interaction of a protein of the invention with its target molecule without the labeling of either the protein or the target molecule. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

Antigen-based heteropolymers that can be tested in the present invention preferentially include a binding moiety that is specific for CR1, preferably human CR1, crosslinked to an antigen that is recognized by an autoantibody. Examples of antigens recognized by autoantibodies include, but are not limited to, any one of the following: factor VIII (antibodies associated with treatment of hemophilia by replacement recombinant factor VIII); the muscle acetylcholine receptor (the antibodies are associated with the disease myasthenia gravis); cardiolipin (associated with the disease lupus); platelet associated proteins (associated with the disease idiopathic thrombocytopenic purpura); the multiple antigens associated with Sjogren's Syndrome; the antigens implicated in the case of tissue transplantation autoimmune reactions; the antigens found on heart muscle (associated with the disease autoimmune myocarditis); the antigens associated with immune complex mediated kidney disease; the dsDNA and ssDNA antigens (associated with lupus nephritis); desmogleins and desmoplakins (associated with pemphigus and pemphigoid); or any other antigen which is well-characterized and is associated with disease pathogenesis.

Exemplary heteropolymers and antigen-based heteropolymers for testing in the instant invention and methods of making them are known in the art. For example, exemplary heteropolymers are taught in WO 03007971A1; U.S. 20020103343A1; U.S. Pat. No. 5,879,679; U.S. Pat. No. 5,487,890; U.S. Pat. No. 5,470,570; WO 9522977A1; WO/02075275A3, WO/0246208A2 or A3, WO/0180883A1, WO/0145669A1, WO 9205801A1, Lindorfer et al. 2001 *J. Immunol. Methods*. 248:125; Hahn et al. 2001. *J. Immnol*. 166:1057; Nardin et al.1998. *J. Immunol. Methods*. 211:21; Kuhn et al. 1998. *J. Immunol*. 160:5088; Taylor et al. 1997. *Cancer Immunol. Immunother*. 45:152; Taylor et al. 1997. *J. Immunol*. 159:4035; and Taylor et al. 1992. *J. Immunol*. 148: 2462. In addition, variant forms of these heteropolymers can be made. For example, in one embodiment, forms of bispecific molecules made using different linking chemistries can be used. Exemplary reagents that can be used to cross-link the components of a bispecific molecule include: polyethelyene glycol, SATA, SMCC, as well others known in the art, and available, e.g., from Pierce Biotechnology. Exemplary forms of bispecific molecules that can be tested are described in U.S. Ser. No. 60/411,731, filed on Sep. 16, 2002, the contents of which are incorporated herein by reference.

In another embodiment, different multimeric forms of bispecific molecules can be made (e.g., dimer, trimer, tetramer, pentamer, or higher multimer forms). In another embodiment, purified forms of bispecific molecules can be tested, e.g., as described in U.S. Ser. No. 60/380,211, filed on May 13, 2002, the contents of which are incorporated herein by reference.

In another embodiment, when one of the binding moieties of the heteropolymer is an antibody, antibodies of different isotypes (e.g., IgA, IgD, IgE, IgG1, IgG2 (e.g., IgG2a), IgG3, IgG4, or IgM) can be used. In another embodiment, portions of an antibody molecule (e.g., Fab fragments) can be used for one of the binding moieties. In a preferred embodiment at least one of the binding moieties is an antibody comprising an Fc domain. In one embodiment, the antibody is a mouse antibody.

In another embodiment, the effect of modifications to antibodies can be tested, e.g., the effect of deimmunization of the antibody, e.g., as described in U.S. Ser. No. 60/458,869, filed on Mar. 28, 2003 can be tested.

Exemplary targeted agents that can be bound by the bispecific compounds of the present invention include blood-borne agents, including, but not limited to, any of the following: viruses, viral particles, toxins, bacteria, polynucleotides, antibodies, e.g., autoantibodies associated with an autoimmune disorder. In one embodiment, exemplary targeted viral agents include, but are not limited to, any one of the following: cytomegalovirus, influenza, Newcastle disease virus, vesicular stomatitus virus, herpes simplex virus, hepatitis, adenovirus-2, bovine viral diarrhea virus, human immunodeficiency virus (HIV), dengue virus, Marburg virus, Epstein-Barr virus.

Exemplary bacterial agents include: *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. hyicus, *Staphylococcus haemolyticus, Staphylococcus hominis, Staphylococcus saccharolyticus.*

In one embodiment, the targeted agent is resistant to traditional therapies, e.g., is resistant to antibiotics.

In another embodiment, exemplary targeted agents that can be bound by the antigen-based heteropolymers of the present invention include, but are not limited to, any one of the following: autoantibodies associated with treatment of hemophilia by replacement recombinant factor VII; autoantibodies associated with the autoimmune diseases myasthenia gravis, lupus, lupus nephritis, idiopathic thrombocytopenic purpura, Sjogren's Syndrome, myocarditis, or pemphigus and pemphigoid; autoantibodies associated with tissue transplantation autoimmune reactions; autoantibodies associated with immune complex mediated kidney disease; or any other autoantibody which is well-characterized and is associated with disease pathogenesis.

In yet other embodiments, exemplary biologic agents that can be bound by the bispecific compounds of the present invention include infectious agents and toxins which can be associated with biowarfare, including, but not limited to, any one of the following: anthrax, smallpox, plague, Ebola, and Marburg virus.

In one embodiment, in performing an assay of the invention, the agent is administered to the transgenic animal, e.g., prior to, simultaneously with, or after administration of a bispecific compound.

The bispecific compounds of the present invention, or any portion thereof, may be modified to enhance their half life. Peptide analogs are commonly used in the pharmaceutical industry as non-peptide drugs with properties analogous to those of the template peptide. These types of non-peptide compounds are termed "peptide mimetics" or "peptidomimetics" (Fauchere, J. (1986) *Adv. Drug Res*. 15:29; Veber and Freidinger (1985) *TINS* p.392; and Evans et al. (1987) *J. Med. Chem* 30:1229, which are incorporated herein by reference) and are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), such as an antigen polypeptide, but have one or more peptide linkages optionally replaced by a linkage selected from the group consisting of: —CH2NH—, —CH2S—, —CH2—CH2—, —CH═CH— (cis and trans), —COCH2—, —CH(OH)CH2—, and —CH2SO—, by methods known in the art and further described in the following references: Spatola, A. F. in *Chemistry and Biochemistry of Amino Acids, Peptides, and Proteins* Weinstein, B., ed., Marcel Dekker, New York, p. 267 (1983); Spatola, A. F., Vega Data (March 1983), Vol. 1, Issue 3, "Peptide Backbone Modifications"; Morley, J. S. (1980) *Trends. Pharm. Sci*. pp.463-468; Hudson, D. et al. (1979) *Int. J. Pept. Prot. Res*. 14:177-185 (—CH2NH—, CH2CH2—); Spatola, A. F. et al. (1986) *Life. Sci*. 38:1243-1249 (—CH2—S); Hann, M. M. (1982) *J. Chem. Soc. Perkin. Trans. I* 307-314 (—CH—CH—, cis and trans); Almquist, R. G. et al. (1980) *J. Med. Chem*. 23:1392-1398 (—COCH2—); Jennings-White, C. et al. (1982) *Tetrahedron Lett*. 23:2533 (—COCH2—); Szelke, M. et al., European Patent Application No. EP 45665 (1982) CA: 97:39405 (—CH(OH)CH2—); Holladay, M. W. et al. (1983) *Tetrahedron. Lett*. 24:4401-4404 (—C(OH)CH2—); and Hruby, V. J. (1982) *Life Sci*. 31:189-199 (—CH2—S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labeling) of peptidomimetics should not substantially interfere with the desired biological or pharmacological activity of the peptidomimetic.

Systematic substitution of one or more amino acids of an amino acid sequence with a D-amino acid of the same type (e.g., D-lysine in place of L-lysine) can be used to generate more stable peptides. In addition, constrained peptides can be generated by methods known in the art (Rizo and Gierasch (1992) *Annu. Rev. Biochem*. 61:387, incorporated herein by reference); for example, by adding internal cysteine residues capable of forming intramolecular disulfide bridges which cyclize the peptide.

Such modified polypeptides can be produced in prokaryotic or eukaryotic host cells. Alternatively, such peptides can be synthesized by chemical methods. Methods for expression of heterologous polypeptides in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y.; Berger and Kimmel, *Methods in Enzymology*, Volume 152, Guide to Molecular Cloning Techniques (1987), Academic Press, Inc., San Diego, Calif.; Merrifield, J. (1969) *J. Am. Chem. Soc*. 91:501; Chaiken I. M. (1981) *CRC Crit. Rev. Biochem*. 11:255; Kaiser et al. (1989) *Science* 243:187; Merrifield, B. (1986) *Science* 232:342; Kent, S. B. H. (1988) *Annu. Rev. Biochem*. 57:957; and Offord, R. E. (1980) *Semisynthetic Proteins*, Wiley Publishing, which are incorporated herein by reference).

Polypeptides can be produced, typically by direct chemical synthesis, and used as a binding moiety of a heteropolymer. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal modifications such as amidation, as well as other terminal modifications, including cyclization, can be incorporated into various embodiments of the test compounds. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others.

V. Screening Assays

The present invention methods, also referred to herein as "screening assays", for identifying candidate or test compounds which reduce the concentration of an agent in the serum and/or circulation of a non-human animal.

In one embodiment, bispecific compounds can be tested for their ability to reduce the concentration of an agent in the serum, circulation and/or tissues of a subject.

The ability of a bispecific compound to reduce the concentration of an agent in the serum, circulation and/or tissues of a non-human animal can be evaluated in a number of different ways. For example, the concentration of an agent in the serum, circulation and/or tissue can be measured directly, e.g., by performing an art recognized assay which allows for enumeration of the agent, e.g., in tissue, blood or serum samples (such as by measuring viral titers, performing colony (e.g., plaque) forming assays, bacterial colony counts, or performing ELISA or other detection assays for toxins or the like).

In methods provided in the present invention, the concentration of an agent, e.g. pathogenic agent, in the serum, circulation and/or tissue of the non-human animal can be reduced by at least e.g. about 20%, about 30%, about 40%, about 50%, about 60%, about 70%, about 80%, about 90% or about 100%.

In another embodiment, the concentration of an agent in the serum, circulation and/or tissue of a subject can be measured indirectly. For example, pathology resulting from the presence of the agent in the serum and/or circulation can be measured, e.g., by examining tissue samples from the animal. Another indirect measurement of the concentration of an agent in the serum, circulation and/or tissue of the non-human animal is measurement of the ability of the agent to cause infection in the non-human animal. For example, the effect of the bispecific compound on clinical signs and symptoms of infection can be measured. The ability of the bispecific compound to inhibit the spread of infection, e.g., from one organ system to another or from one individual to another can also be tested.

In another embodiment the ability of the bispecific compound to bind to cells bearing CR1 in the non-human animal is measured. For example, in one embodiment, determining the ability of the bispecific compound to bind to a CR1 target molecule can also be accomplished using a technology such as real-time Biomolecular Interaction Analysis (BIA) (Sjolander, S. and Urbaniczky, C. (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In another embodiment, the destruction of the agent by cells in the non-human animal (e.g., killing by macrophage) is measured.

Compounds that reduce the concentration of the agent in the serum and/or circulation of the non-human animal (as compared with concentrations observed in non-human animals that do not receive the bispecific compound) can be selected.

Compounds for testing in the subject assays can be selected from among a plurality of compounds tested. In another embodiment, bispecific compounds for testing in the instant assays may have already been identified as being capable of binding CR1, e.g., in an in vitro assay and may be further evaluated or optimized using the instant assays. In such cases, the ability of a bispecific compound to reduce the concentration of an agent in the serum and/or circulation can be compared to another bispecific compound or a non-optimized version of the same compound to determine its ability reduce the concentration of the agent in the serum and/or circulation.

In preferred embodiments, the bispecific compounds of the instant invention are administered at concentrations in the range of approximately 1 μg compound/kg of body weight to approximately 100 μg compound/kg of body weight. As defined herein, a therapeutically effective amount of a bispecific compound (i.e., an effective dosage) ranges from about 0.01 to 5000 μg/kg body weight, preferably about 0.1 to 500 μg/kg body weight, more preferably about 2 to 80 μg/kg body weight, and even more preferably about 5 to 70 μg/kg, 10 to 60 μg/kg, 20 to 50 μg/kg, 24 to 41 μg/kg, 25 to 40 μg/kg, 26 to 39 μg/kg, 27 to 38 μg/kg, 28 to 37 μg/kg, 29 to 36 μg/kg, 30 to 35 μg/kg, 31 to 34 μg/kg or 32 to 33 μg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, the animal is treated with bispecific compound in the range of between about 1 to 500 μg/kg body weight following intravenous (iv) injection of an agent. It will also be appreciated that the effective dosage of a bispecific compound used for treatment may increase or decrease over the course of a particular treatment. Changes in dosage may result and become apparent from the results of diagnostic assays as described herein.

The route of administration of test compounds and/or agents can be intravenous (iv) injection into the circulation of the animal. Other administration routes include, but are not limited to, topical, parenteral, subcutaneous, or by inhalation. The term "parenteral" includes injection, e.g. by subcutaneous, intravenous, or intramuscular routes, also including localized administration, e.g., at a site of disease or injury. Sustained release of compounds from implants is also known in the art. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration are performed according to art-accepted practices.

The candidate compounds and agents can be administered over a range of doses to the animal. When the agent is also administered to the animal, the candidate compound can be administered either before, at the same time, or after, administration of the agent.

CR1 expressing transgenic animals, e.g. mice, of the present invention can be used to screen or evaluate candidate compounds useful for treating disorders or diseases in humans that are associated with the presence of unwanted agents in the serum and/or circulation of a subject, such as autoantibodies, infectious agents, or toxins.

In one embodiment, the subject screening assays can be used to evaluate the activity of a bispecific compound to reduce the concentration of an agent from the serum and/or circulation. For example, the ability of different forms of bispecific compounds (e.g., dimer, trimer, tetramer, pentamer, or higher multimer forms) to reduce the concentration of an agent from the serum and/or circulation can be tested.

In one embodiment, the activity of heteropolymers or antigen heteropolymers can be compared to conventional bispecific antibodies.

In an additional embodiment, the activity of heteropolymers or antigen heteropolymers can be compared to suitable controls, including saline and/or irrelevant HP (e.g., in a preferred example of the instant invention, ΦX-PA).

In another embodiment, the ability of bispecific compounds prepared using different linking chemistries can be compared for their ability to reduce the concentration of an agent in the serum and/or circulation. For example, in one embodiment, one moiety of bispecific compound can be linked to the second moiety using an SMCC/SATA linkage or a PEG/SATA linkage. In another embodiment, the subject transgenic animals can be used to determine whether a specific linking chemistry causes an immune response in the animal.

In yet another embodiment, the subject animals and assays can be used to select preferred antigen binding moieties (e.g., monoclonal antibodies having particular binding specificities) for use in making optimized bispecific compounds.

In still another embodiment, binding moieties which bind to CR1, but which are not antibodies can be tested.

In a further embodiment, the half life of different bispecific compounds can be tested and optimized. For example, in one embodiment, the half-life can be modified by using different antibody isotypes or fragments of antibodies. In addition, novel ways of modifying the half-life can be determined.

In another embodiment, the in vivo pharmocokinetics of various multimeric forms or differently linked forms of bispecific compounds can be compared.

In another embodiment, the subject transgenic animals can be used in evaluating in vivo models for efficacy of bispecific compounds in the treatment of animals exposed to, e.g., toxins, viruses, bacteria, or which have an autoimmune condition.

In another embodiment, the subject screening assays can be used to evaluate various delivery routes and formulations of bispecific compounds to optimize treatment of a subject.

In another embodiment, the subject assays can be used to determine whether bispecific compounds enhance immune responses in an animal. In another embodiment, the subject animals and assays can be used to evaluate the mechanism of transfer of bispecific compounds to cells bearing CR1 in the animal and to evaluate the effect of antibody affinity for CR1 on the activity of the bispecific compound.

In a further embodiment, the subject animals and screening assays can be used to determine correlations between in vitro assays and in vivo biological effects in order to validate certain forms of in vitro testing.

Therapeutic compounds identified or optimized by methods of the present invention may be used in either prophylactic or therapeutic applications, and can be used alone or in combination with other known treatments, e.g., vaccines, antibiotics, anti-viral agents, anti retro-viral agents (agents that inhibit viral replication). In one embodiment, a subject is treated after exposure to an agent. In another embodiment, a subject is treated prior to exposure to an agent. In one embodiment, the subject can be treated repeatedly (as needed) with a bispecific compound. In yet another embodiment, treatment with a bispecific compound of the invention (whether prior to or after exposure to an agent) results in a lasting immune response to the agent, thereby reducing or eliminating the need for further treatments.

This invention is further illustrated by the following examples which should not be construed as limiting. The contents of all references, patents and published patent applications cited throughout this application are incorporated herein by reference.

EXAMPLES

The following materials and methods were used in the examples.

Materials and Methods mAbs, HPs, and phage. The following murine monoclonal antibodies (mAb) were used: anti-CR1 mAb YZ-1 (IgG1), which binds LHR-A, -B, and -C (Nickells et al. *Clin Exp Immunol* 112, 27-33); anti-CR1 mAb 543 (American Type Culture Collection), which binds LHR-C and -D; and anti-CR1 mAb 7G9 (IgG2a), which binds LHR-A, -B, and -C (Nickells et al. *Clin Exp Immunol* 112, 27-33), was purified from ascites (Pincus et al. *Clin Immunol* 105,141-54) made from the hybridoma; anti-ΦX174 mAb 7B7 (IgG2a; Taylor et al. *J Immunol* 158, 842-850) and anti-anthrax protective antigen mAb 14B7 (IgG2a; Little et al. *Infect Immun*. 56, 1807-1813) Bacteriophage ΦX174 (designated ΦXcs70am-3 ATCC Number 49696-B1) was obtained from American Type Culture Collection (Manassas, Va.) and phage stocks were produced by Pan Vera Invitrogen (Carlsbad, Calif.).

Anti-CR1 mAb 7G9 was linked to anti-ΦX174 mAb 7B7 (ΦX-CR1 HP) by a thioether linkage using either SMCC (sulfosuccinimidyl 4-(N-maleimidomethyl) cyclohexane-1-carboxylate), and SATA-(N-succinimidyl-S-acetylthioacetate) (Pierce Biotechnology, Rockford, Ill.) activated antibodies as previously described (Lindorfer et al. *J Immunol* 167, 2240-2249). A modification of the above method was developed to make PEG HP, wherein instead of activating one mAb with SMCC, a biologically inactive linker/spacer molecule (modified polyethylene glycol ~5000 MW) containing a maleimide group via an NHS ester was used, and this modified mAb was reacted with a SATA activated mAb. A non CR1-binding HP (ΦX-PA HP) was produced by SMCC/SATA linkage of mAb 7B7 to mAb 14B7.

Generation of transgenic mouse. An expression plasmid for the human CR1 gene was constructed by obtaining a 9.9 kb Not I DNA fragment containing the complete cDNA encoding the common allele of human CR1 (hCR1; Klickstein et al. *J Exp Med* 168, 1699-1717). This fragment was inserted into the unique Not I site of plasmid pGATA-1, placing hCR1 under the transcriptional control of the erythroid specific promoter GATA1 (Visvader et al. *Genes Dev*. 12, 473-479). Orientation of the CR1 gene was confirmed by sequencing. The GATA1-CR1 transgenic construct was digested with Sal I, and the promoter/CR1 gene fragment (approximately 22 kb) was purified and microinjected into fertilized eggs of SJL mice, which were then implanted into C57BL/6 foster mothers. The resulting progeny were screened for integration of the transgene by PCR using mouse tail DNA and maintained by mating with C57BL/6 mice. Positive heterozygotes were detected by PCR analysis of DNA and by expression analysis on erythrocytes by FACS analysis as described below.

Isolation of high molecular weight DNA from mouse tails was done with Easy-DNA kit (Invitrogen) according to the manufacturers protocol. Approximately 1 μg of DNA was subjected to 35 cycles of amplification on a thermal cycler. The two transgenic specific primers used for PCR analysis of transgenic mice GATA-1 forward primer (5'-ACCCTTTCT-GTCCTCACA-3'; SEQ ID NO: 1) and CR1 gene reverse primer (5'-TTTCTCCCTCCGCTTCCAGGTTG-3'; SEQ ID NO: 2) produced a 653-bp DNA fragment (FIG. 1*a*). PCR products were resolved by electrophoresis in 1% agarose gels.

Baboons. Baboons were used under contract with IACUC approval from the colony maintained at SouthWest Foundation for Biomedical Research (San Antonio, Tex.). Prior to the study, blood was obtained from 40 animals and analyzed for the level of CR1 expression by FACS as described below. The results were used to select animals with 1800-3600 CR1/E for inclusion into the study.

Erythrocytes. Citrate anticoagulated mouse blood was obtained from the tail vein and following centrifugation at 500×g the buffy coat layer was removed and the E were washed 3 times in Hank's balanced salt solution, without calcium and magnesium ($HBSS^{-}$) (Gibco/Invitrogen, Grand Island, N.Y.). Human E from normal donors were obtained from acid-citrate anticoagulated venous blood, which was diluted with equal volume of HBSS with 0.001 M EDTA, 0.01% gelatin. Following centrifugation and removal buffy coat layer, the cells washed several times in the above buffer. Finally, the cells were resuspended in HBSS containing calcium and magnesium and 0.01% gelatin ($HBSS^{++}$/gelatin). All E for immune complex binding assays were used on the day of collection, and were standardized on the basis of hemoglobulin concentration, such that a 1/30 dilution of cells in water gave a hemoglobin absorbancy of 0.64 at 414 nm.

Human serum. Two ml of serum (from the donor of human E) was made 5 mM EDTA chilled to 4° C., and mixed with the washed membranes from approximately $10^6$ wt mE for 60 min to absorb out human anti-mouse E immunoglobulins.

Subsequently the absorbed human serum was centrifuged at 15,000×g to remove the mouse membranes, and the supernatant was aliquoted for storage at −80° C. until use for opsonizing immune complexes.

Immunoblotting for CR1. E from 100 μl blood were washed twice in HBSS⁼ and then lysed overnight in ghosting buffer (5 mM sodium phosphate (pH 8.0), 1 mM EDTA, and 1/100 dilution of "Protease Inhibitor Cocktail" (Sigma, St. Louis, Mo.). The membranes were solubilized in SDS-sample buffer (Boston Bioproducts, Boston, Mass.), boiled for 5 min, and resolved unreduced on a 4-12% NuPage gradient gel (Invitrogen, Carlsbad, Calif.). Proteins were transferred onto Hybond nitrocellulose membrane (Amersham Biosclences, Arlington Heights, Ill.). The membranes were immunoblotted with anti-CR1 mAb YZ-1, followed by incubation with peroxidase-conjugated goat anti-mouse secondary antibody (Vector Laboratories, Burlingame, Calif.). Blots were visualized with SuperSignal West Pico Chemiluminescence substrate (Pierce Biotechnology).

FACS analysis of CR1 expression on the surface of E. Anti-CR1 mAb 7G9, was labeled with Alexa 488™ (Molecular Probes, Eugene, Oreg.) following the manufacturer's directions. Wild type mE, or mE+CR1 or hE were suspended to a concentration of 1% in PBS/1% BSA buffer (PBS/BSA). Alexa 488-7G9 (100 μl of a 2 μg/ml stock) was added to 100 μl of the E and incubated for 30 min at room temperature. Unbound Alex-7G9 was removed by washing twice with PBS/BSA. E were selectively gated on by flow cytometry based on their forward scatter versus side scatter profile and 20,000 events were analyzed within that gate using a FACS-Calibur™ instrument and CellQuest Pro software, V3.3 (BD Biosciences, San Jose, Calif.).

Distribution of CR1 on mouse and human E. Human or mouse blood was diluted in HBSS⁼/BSA and the E were resuspended in the same buffer at a concentration of 10% (V/V). Anti-CR1 mAb 543 was added to E, followed by Alexa 488 labeled goat anti-mouse (Molecular Probes) such that the final concentrations of antibody and E were 5.0 μg/ml and 5% respectively. After incubation for 30 min at 37° C., the unbound mAb was removed by centrifugation and washing. Light and fluorescence microscopy was performed using an Olympus BX40F4 microscope (Olympus America Inc., Melville N.Y.) at a 1000×magnification.

Immune complex and HP binding to E in vitro. BSA, Fraction V (Sigma) (1 mg/ml) was labeled with FITC (Aldrich Chemical, Milwaukee, Wisc.) and dialyzed to remove unbound FITC. The assumed concentration of BSA after labeling was 0.8 mg/ml. Mixing 30 μg FITC-BSA and 100 μl of rabbit-anti-BSA IgG (Molecular Probes) a in final volume of 250 μl for 60 min at 37° C. allowed the formation of immune complexes. Thirty μl of the immune complexes were aliquoted into microfuge tubes, followed by the sequential addition of 40 μg of absorbed human serum, 4 μl stock cations (30 mM $CaCl_2$. 100 mM $MgCl_2$) and 150 μl E suspension. After incubation for 15 min at 37° C. to allow both the opsonization of the immune complexes and the binding of the opsonized immune complex to E, the mixtures were transferred to 12×75 mm tubes containing 3 ml of cold HBSS-0.01% gelatin and centrifuged at 400×g and resuspended in 3 ml of the same buffer. The cells were analyzed on a FACSscan™ and 10,000 events were recorded using CellQuest Pro software V4.01.

Binding of SMCC-HP to E was determined in the following manner. Parental mE or mE+CR1 or hE was suspended to a concentration of 10% in PBS/−BSA buffer. HP (20 ng) was added to 100 μl of the E for 15 min at 37° C. with shaking. Unbound HP was removed by washing twice with PBS/BSA buffer. Goat anti-mouse IgG-Alexa 488 (Molecular Probes) at 10 μg/ml was added to the tubes and incubated for 30 min at room temperature followed by two washes with PBS/BSA buffer. Flow cytometry was then performed (FACSCallibur) on the samples and the E were selectively gated based on their forward scatter versus side scatter profile and 20,000 events were analyzed within that gate.

In vivo phage clearance. Baboons (8-10 kg) were injected with $1.5\times10^{11}$ PFU iv and 20 minutes later injected iv with 0.3 mg of ΦX-CR1 HP (PEG and SMCC), ΦX-PA HP or an equivalent volume of saline. Blood samples were obtained by femoral venipuncture into tubes containing EDTA (0.01M final concentration) as anticoagulant, centrifuged, and the plasma frozen at −70° C. Plasma phage were determined by plaque assay as previously described (Taylor et al. *J Immunol* 158, 842-850).

Mice were injected iv in a 0.1 ml volume at a dose of $3\times10^7$ PFU/animal. Saline control, HPs or irrelevant HP (1, 6, or 12 μg) were injected iv in a 0.1 ml volume 45 min later. Blood samples (50 μl) were collected from the tails of mice into 0.5 ml Alsever's solution containing 0.04M EDTA at various time points, pre or post HP administration as defined in FIG. 6*b*. Plasma was separated from cells and stored at 4° C. Plasma phage were determined by plaque assay as previously described (Taylor et al. *J Immunol* 158, 842-850).

Example 1

Construction of Expression Construct Containing Nucleotide Sequence Encoding Human Complement Receptor 1 (CR1) Polypeptide Operably Linked to a GATA-1 Promoter In order to express human CR1 on murine erythrocytes, it was necessary to identify a promoter that would provide for mouse erythrocytes. The regulatory sequences of the murine GATA-1 gene had previously been employed to express several genes selectively in hematopoietic tissues in transgenic mice (McDevitt, M. A. et al., (1997) Proc. Natl. Acad. Sci., USA, 94:7976-7981; Visvader J. E. et al., (1998) Genes & Dev. 12(4):473-479). The transcription factor GATA-1 is expressed in several hematopoietic lineages and multipotential progenitors, and is required for the development of red blood cells and platelets. Specific control elements upstream of the GATA-1 gene, which were defined by their DNase I hypersensitivity in the context of erythroid chromatin, were identified that enhance overall transgene expression in transgenic mice and confer activation specifically within the primitive erythroid cells, thereby recapitulating the pattern of GATA-1 developmental expression (McDevitt, M. A. et al., (1997) Proc. Natl. Acad. Sci., USA, 94:7976-7981). This transgene cassette was subsequently used to re-introduce and express the murine stem cell leukemia gene (SCL/tal-1) in an SCL knockout mouse; the SCL gene is normally expressed specifically in hematopoietic cells, vascular endothelium and the developing brain, and the murine GATA-1 regulatory sequences allowed rescue of the hematopoietic defect of SCL-/-embryos (Visvader J. E. et al., (1998) Genes & Dev. 12(4):473-479). It was therefore possible that these murine GATA-1 regulatory sequences could be used to direct expression of the human CR1 gene on mouse erythrocytes.

A construct containing the murine GATA-1 regulatory sequences (proximal promoter, downstream intron sequences, and upstream hypersensitive sites) together with the rabbit globin poly(A) addition region and SV40 sequence was used (Visvader and Orkin. 1998. *Genes and Development*. 12:473).

The plasmid piABCD containing a cDNA encoding for functional human CR1 was obtained from Dr. Lloyd Klickstein (Wilson J. G. et al, (1986) J. Exp. Med. 164:50-59; Klickstein L. B. et al. (1988) J. Exp. Med. 168:1699-1717). A 6,860 bp fragment of piABCD encoding CR1 was cloned into the NotI site of the plasmid containing the murine GATA-1 regulatory sequences (>15,000 bp of genomic murine GATA-1 gene extending from ~10,000 bp upstream of ATG I in exon 2 (5+ kb upstream of start of transcription) to 3' of the gene). After transformation, a clone with the correct orientation was selected and confirmed by sequencing according to methods commonly known in the art. Briefly, the whole insert was excised from the vector using the SalI site. The plasmid pSc-3Z (4.7 kb, low-copy plasmid, amp) was used. DNA was purified by a CsCl gradient and then digested with SalI to provide a 15,000 bp fusion gene encoding the GATA-1 promoter and the CR1 gene (FIG. 1*a* shows a schematic map of the GATA1/hCR1 transgenic construct, wherein 7 kb of GATA1 upstream sequence and ~1.5 kb of sequence downstream of exon 3 flank the hCR1 cDNA. Numbered regions of FIG. 1*a* indicate exons of GATA-1. The endogenous GATA-1 initiation of translation codon in exon 2 was replaced with a Not I site. The cDNA for hCAR1 was inserted at this Not I site. A polyadenylation signal from simian virus 40 (pA) lies 3' of the cDNA insert. The PCR primers used to detect the transgene consisted of a forward primer specific for GATA-1 exon 2 and a reverse primer specific for hCR1 sequence (arrowheads in FIG. 1*a*)) The fusion gene was then purified and subsequently used to create transgenic mice.

Example II

Construction of Transgenic Mouse whose Genome Contains Nucleotide Sequence Encoding Human Complement Receptor 1 (CR1) Polypeptide Operable Linked to a GATA-1 Promoter Transgenic mice were constructed by introducing a 15,000 bp fusion gene encoding the GATA-1 promoter and the CR1 gene by pronuclear injection into B6/129 F1 mouse zygotes, according to methods commonly known in the art, as set forth above. Mice were screened for presence of the foreign fusion gene by removing a portion of the tail and extracting the genomic DNA. PCR analysis on DNA isolated from mouse tail biopsy confirmed generation of founder mice and offspring that were germline transgenic for the GATA1/hCR1 construct. Such mice were identified by a diagnostic 653-bp PCR product (FIG. 1*b*, wherein lane 1 shows the PCR result of a distilled water control as template, while lane 2 displays a PCR assay result using genomic DNA of the transgene mouse as template; M corresponds to a 1-kb ladder marker; lane 3 shows the PCR result for plasmid DNA containing the transgene; and lane 4 displays an assay result wherein genomic DNA of a known nontransgenic mouse was used as template).

Example III

Figure 2:
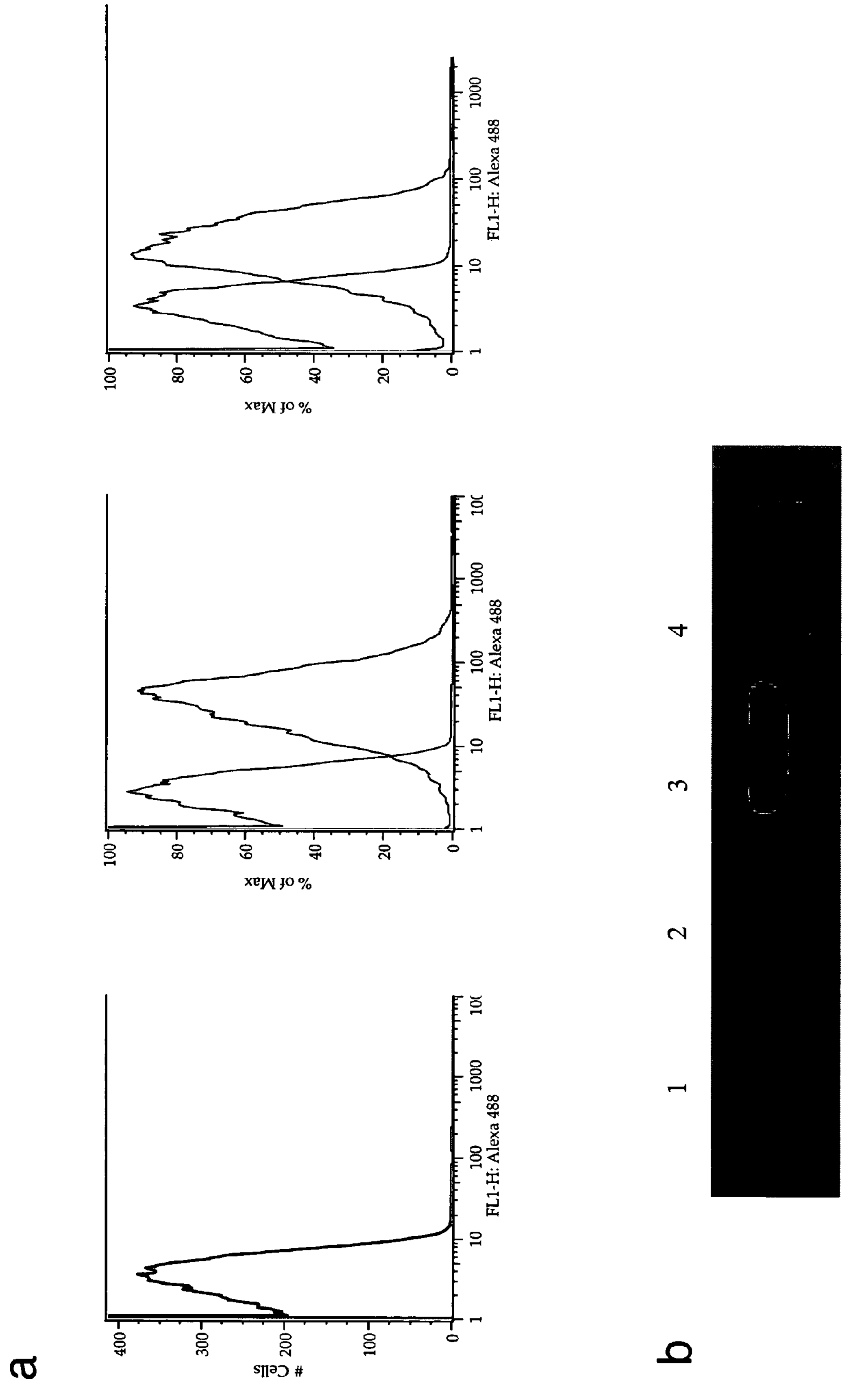
FIG. 2 presents confirmation that E from the transgenic mouse expressed human CR1 antigen of appropriate molecular size.

Evidence of Expression of Human Complement Receptor CR1 on Transgenic Mouse E To confirm that CR1 antigen was expressed on the surface of the E from transgenic mice, flow cytometry was performed after staining hE, mE and mE+CR1 cells with Alexa-488 conjugated anti-CR1 mAb 7G9 (FIG. 2*a*). Analysis confirmed that CR1 antigen was expressed on the surface of hE (right panel) and on mE from the transgenic mouse (center panel), but not on mE from wild type (wt) mice (left panel). Human E (hE, right panel), which were used as a positive control, expressed about 50% of the CR1 on the mE+CR1).

To confirm that the CR1 of mE+CR1 was of an appropriate size, immunoblotting was performed (FIG. 2*b*). E from wt mice, CR1 transgenic mice, and a normal human were lysed and the solubilized, non-reduced membrane proteins resolved on SDS-PAGE. Following transfer the blot was reacted with anti-CR1 mAb YZ-1, as described in Materials and Methods. The human donor was presumed to be heterozygous for the common allele CR1*1 producing a 200 kDa band and the CR1*3 allele producing a 190 kDa band (FIG. 2*b*, lane 4; reviewed in Klickstein, L. B. & Moulds, J. M. in *The Complement Facts Book* (eds. B. J. Morley & M. J. Walport), pp. 136-145). CR1 on E from the transgenic mouse (FIG. 2*b*, lane 3) was similar in molecular weight to the hE CR1 CR1*1 allele, which was consistent with the transgene. No CR1 antigen was detected by YZ-1 mAb in the lysate of wt mE (FIG. 2*b*, lane 2); and a prestained myosin 207 kDa MW marker is shown in FIG. 2*b*, lane 1.

To define the distribution of the GATA-1 promoted CR-1 in the transgenic mice, tissues from the transgenic mouse were fixed by Paragon Biotech (Baltimore, Md.) by standard procedures, stained with anti-CR1 mAb, and examined for the expression of CR1. No tissues were found to be CR1 immunoreactive.

Example IV

Fluorescence Microscopic Analyses Confirmed a Cluster Distribution of CR1 on hE and mE+CR1

Figure 3:
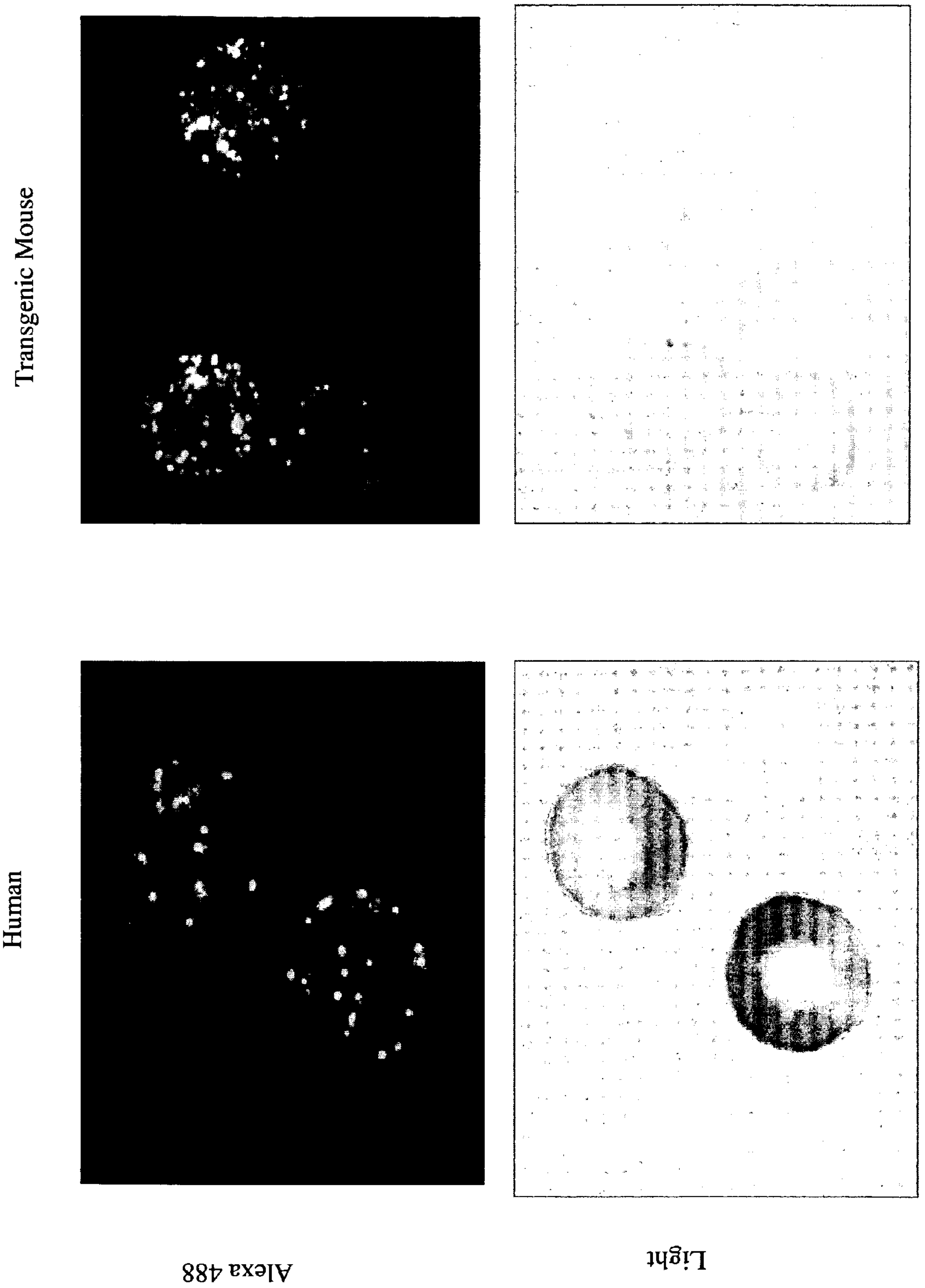
FIG. 3 reveals the distribution of CR1 on mouse and human E.

As the average level of CR1 per hE is quite low (100-1,000/E), and the affinity of monovalent complement ligands for CR1 is low, it is hypothesized that clusters of CR1 are required to effectively ligate a complement opsonized particle to a hE (Klickstein et al. *Immunity* 7, 345-355; Edberg et al. *J Immunol* 139, 3739; Paccaud et al. *J Immunol* 141, 3889-3894; Chevalier and Kazatchkine, *J Immunol* 142, 2031-2036). Thus, the utility of the transgenic mouse as a model of immune adherence-mediated clearance might depend on the CR1 being in clusters on the mE+CR1. hE (FIG. 3, left panels) and mE+CR1 (FIG. 3, right panels) were reacted with anti-CR1 mAb 543 followed by Alexa 488 labeled secondary antibody and viewed by light (FIG. 3, lower panels) and fluorescent microscopy (top panels). CR1 appeared in clusters on hE, as expected (FIG. 3, left panel). The same procedure was repeated for mE+CR1 and the CR1 also appeared in clusters (FIG. 3, right panel) that were consistently smaller but more abundant than the CR1 clusters on hE.

Example V

Ability of mE+CR1 to Bind Opsonized FITC-Labeled Immune Complexes and HP

To test the functionality of the CR1 protein on mE+CR1, the ability of these E to bind opsonized immune complexes was examined. FITC labeled immune complexes consisting of FITC-BSA and rabbit anti-BSA were opsonized with complement by incubation with human serum and allowed to react with E. The samples were then analyzed by flow cytometry. Binding of immune complexes to cells was demonstrated by a positive shift in fluorescence and this was seen only when the immune complexes were opsonized, and the E expressed CR1, i.e. either hE or transgenic mE+CR1 (FIG. 4*a*, wherein the left panel presents results for normal human E (hE); Middle panel, wild type mouse E (mE); Right panel, from transgenic mouse which express human CR1 (mE+CR1). The blue histogram represents E washed in buffer. FITC labeled immune complexes were made and subsequently reacted with buffer (red histogram) or normal human serum (green histogram) in the presence of E. A shift in fluorescence indicated the binding of immune complexes to E, and this was only seen when the immune complexes were opsonized with serum (green histogram), and expressed CR1 (hE or mE+CR1, but not wt mE)).

Figure 4:
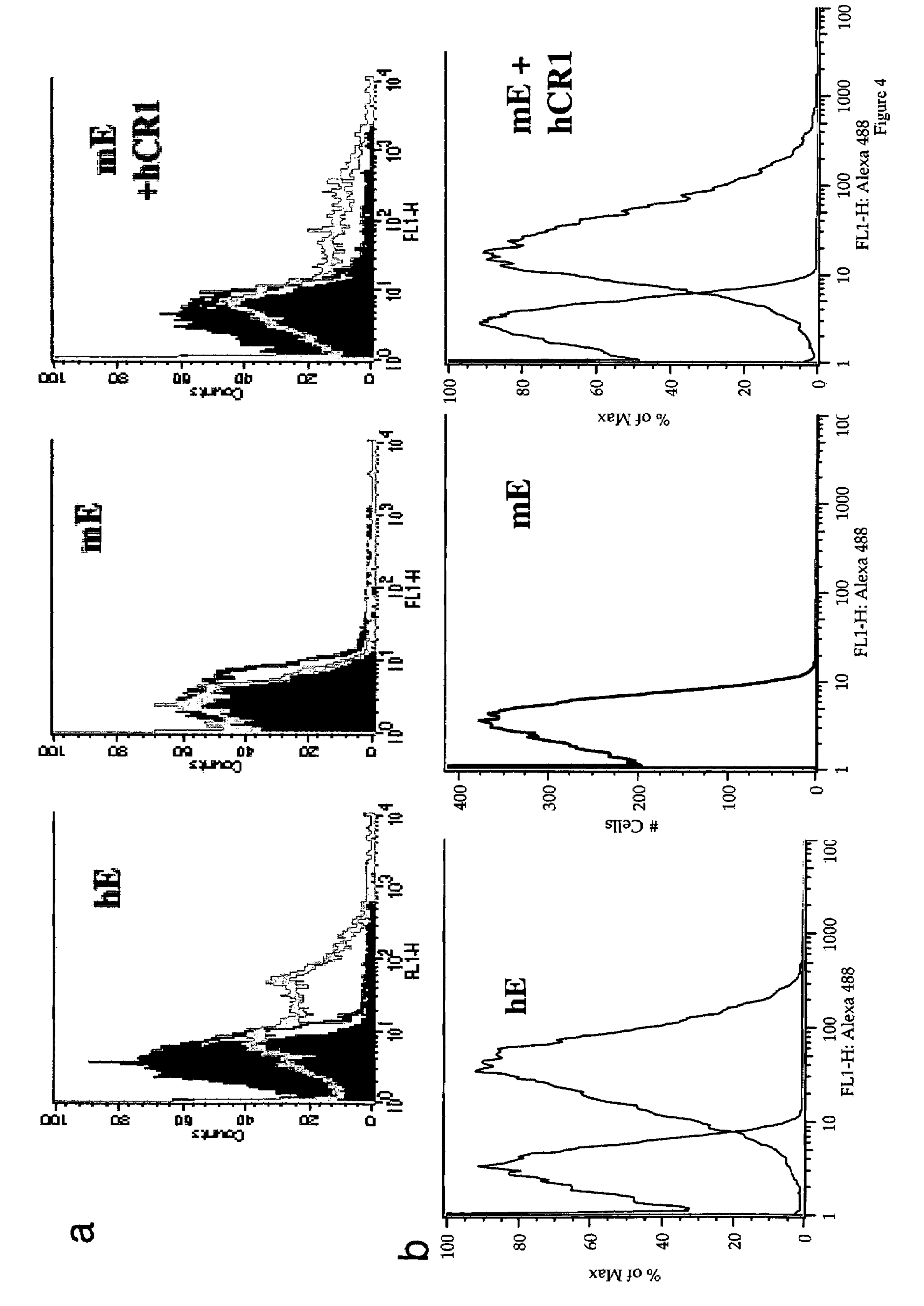
FIG. 4 displays the ability of mE+CR1 to bind human complement opsonized immune complexes or HP.

The ability of E to bind HP was examined by staining HP bound to E with Alexa 488 goat-anti-mouse antibody and analysis by flow cytometry (FIG. 4*b*). Binding of HP was seen when HP was incubated with hE and mE+CR1, but not to wt mE. It is of note that while the hE and the mE+CR1 did not uniformly bind the native immune complexes (FIG. 4*a*), the HP bound to the total populations of hE and mE+CR1 (FIG. 4*b*).

Example VI

Effect of Dose and Type of HP on Phage Clearance in vivo

HP can be used for the clearance of pathogens and toxins from the bloodstream. The CR1 transgenic mouse was designed as a model for testing the efficacy of HP that couples a potential pathogen to erythrocyte CR1 for clearance. Bacteriophage ΦX 174 was used as a model organism for these experiments because, due to a lack of its receptor on mammalian cells, it is not pathogenic for mammals (Och et al. *J Clin Invest* 50, 2559-2568), and it is easily quantified by plaque assay. HP, designated ΦX-CR1, consisted of an anti-ΦX174 mAb (7B7) chemically linked to an anti-CR1 mAb (7G9) using two different chemistries, SMCC or PEG (see Methods). Fluorescence analysis confirmed that the ΦX-CR1 HP bound to both hE and mE+hCR1 but not to wild type mE (FIG. 4*b*). Control HP, designated ΦX-PA, was made by coupling the anti-ΦX174 mAb to a mAb against anthrax protective antigen (PA, 14B7 mAb). ΦX-PA HP, which did not bind to hE or mE+CR1, was used as a control to determine the rate of soluble HP-mediated clearance. This rate represented the sum of fluid phase viral neutralization plus the clearance (of the large HP components) induced by the intrinsic platelet-dependent immune adherence pathway of the mouse.

Figure 5:
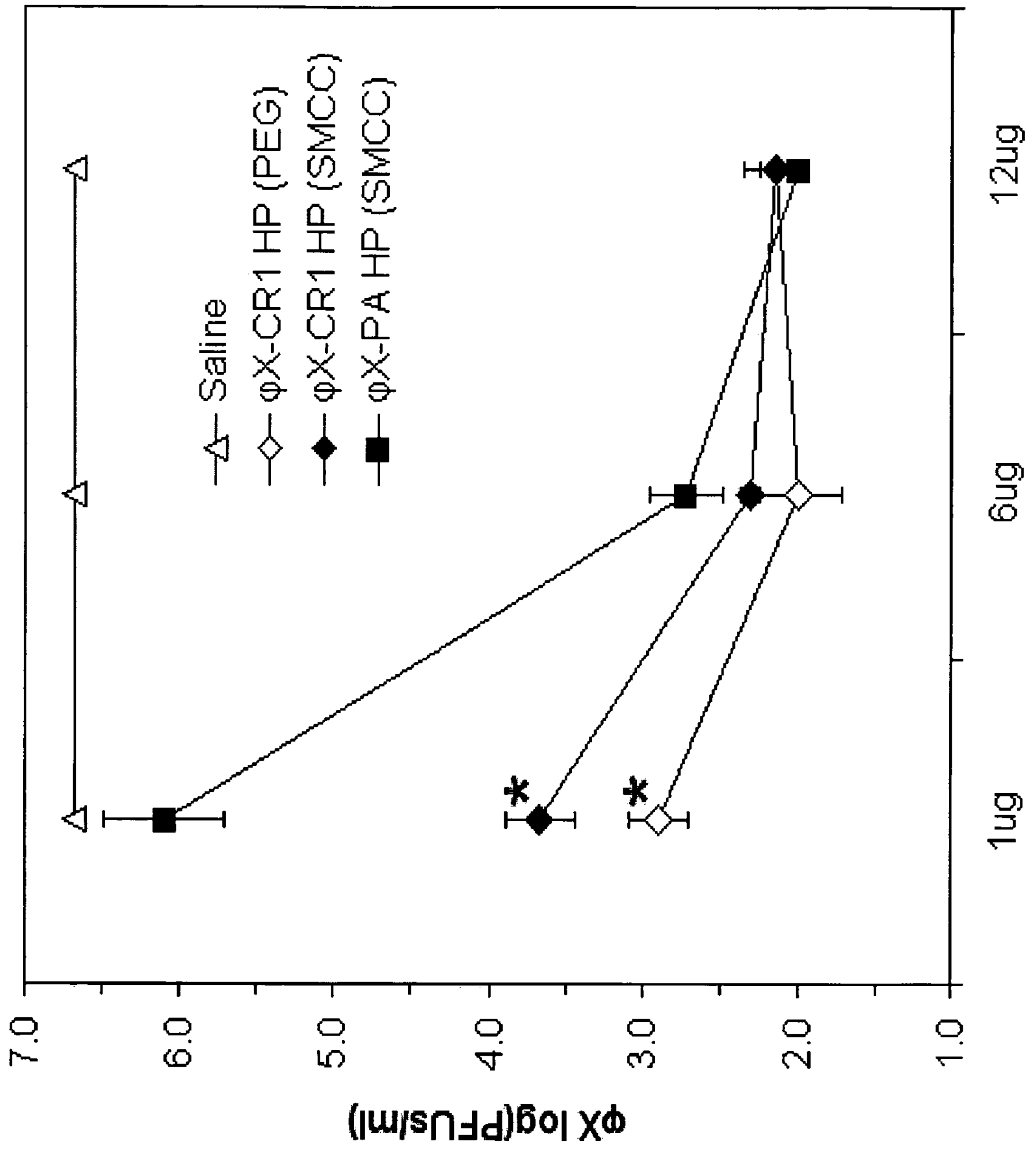
FIG. 5 displays the effect of HP dose on phage clearance in vivo.

Transgenic mice were infused iv with bacteriophage ΦX174 at a dose of $3\times10^7$ PFU/mouse, followed 45 minutes later by either PEG or SMCC HP at three different doses (1.0 μg 6 μg, or 12 μg/mouse), or saline as a negative control. The transgenic mice were bled 24 hrs later to determine PFU of phage per ml of plasma. At 1 μg HP/mouse there was a clear difference in phage reduction in sera with both PEG and SMCC linked forms of ΦX-CR1 HP (3.8 or 3.0 log), as compared with the ΦX-PA HP (0.6 log). ΦX-PA HP became more effective at phage neutralization at higher dose of ΦX-PA HP and ΦX-CR1 HP (6 and 12 μg HP/mouse, FIG. 5, wherein the graph represents the $\log_{10}$ of the phage PFU/ml present in blood sampled from the tails of the mice 24 hours after HP injection. Error bars represent standard errors of the means, n=3. Asterisks indicate significant difference from the ΦX-PA HP at a $p<0.01$ by student's t-test).

Example VII

Figure 6:
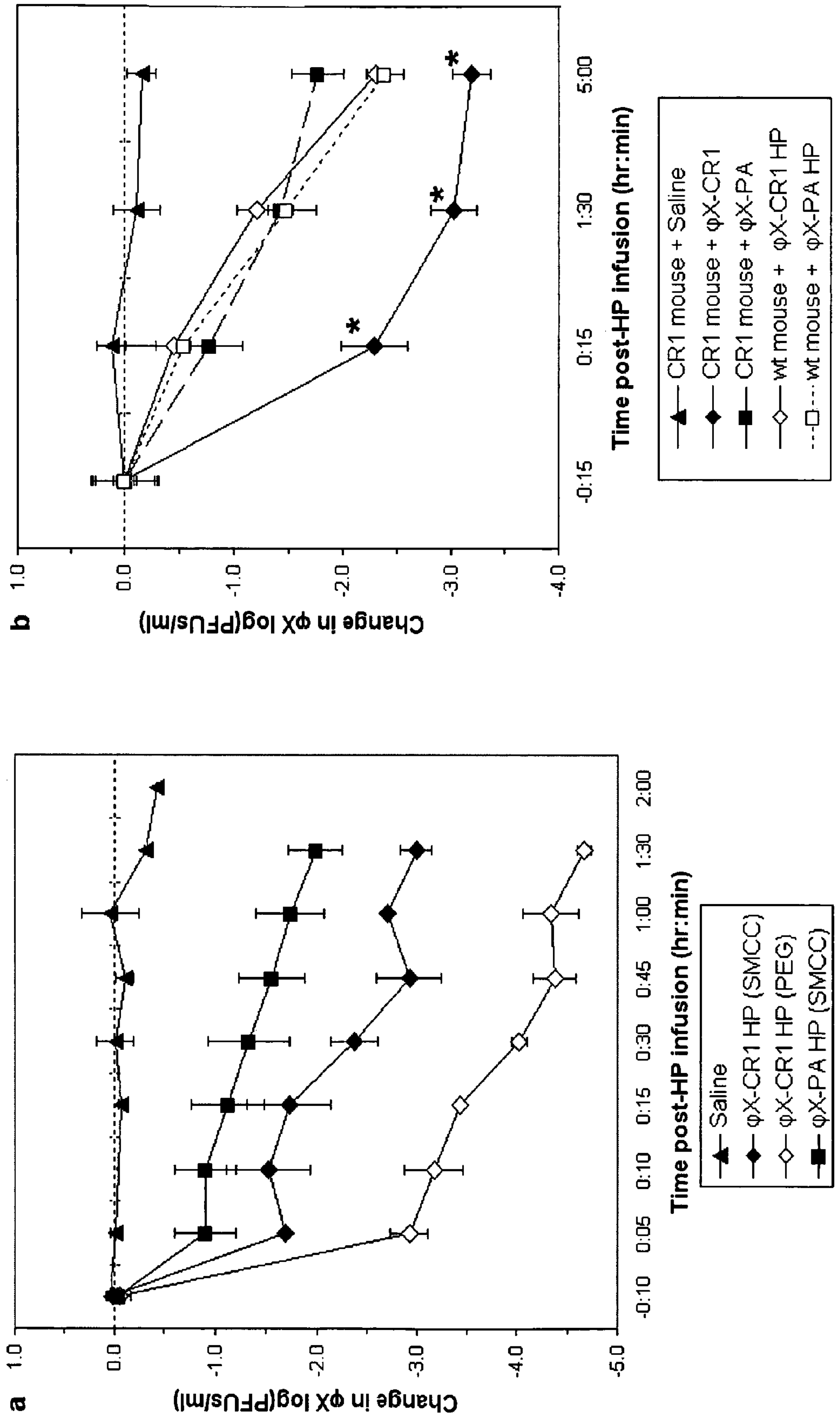
FIG. 6 shows phage clearance results for HPs in baboons, CR1-transgenic and wt mice.

Kinetics of HP-Mediated Clearance of Bacteriophage ΦX174 from the Plasma of Baboons and CR1 Transgenic Mice Because higher primates have CR1-expressing erythrocytes (reviewed in ref #30) these animals have been used in small studies of the efficacy of HP-mediated clearance of various types of particles (Taylor et al. *J Immunol* 148, 2462-2468; Craig et al. *Clin Immunol* 92, 170-180; Nardin et al. *Mol Immunol* 36, 827-835; Lindorfer et al. *J Immunol* 167, 2240-2249), including ΦX174 phage (Taylor et al. *J Immunol* 158, 842-850). Before measuring the kinetics of clearance in the transgenic mice, it was desirable to assess how efficiently the HP of the instant invention functioned in baboons, as such studies would evaluate the predictability of the transgenic mouse model. ΦX174 ($1.5\times10^{11}$ PFU) was infused at t=−20 minutes. At t=0 minutes, 20 minutes later, SMCC- or PEG-linked ΦX-CR1 HP, or non-E binding SMCC-linked ΦX-PA HP, or saline as a negative control were infused in baboons. HP were used at 0.3 mg/animal (8-10 kg each), a dose roughly equivalent to the 1 ug/mouse dose on a per weight basis. Sampling of venous blood (performed 15 and 10 min pre HP infusion and at multiple time points (5-90 min) post HP infusion) over the following 100 minutes revealed two phases of clearance (refer to FIG. 6*a*). The first was a rapid initial phase resulting in clearance of 3.0 logs by the ΦX-CR1 PEG HP, 1.6 log by ΦX-CR1 SMCC HP, and 0.8 log by the control ΦX-PA HP by 5 minutes post HP infusion. The slower second phase from 5 to 90 minutes post HP infusion resulted in clearance of ~1.5 log/85 minutes for ΦX-CR1 HP (PEG), ~1.0 log/85 minutes for ΦX-CR1 HP (SMCC), and a ~1.0 log/85 minutes for ΦX-PA HP. The graph of FIG. 6*a* represents the reduction in phage titer seen in blood at various times post treatment [Due to limitations in the number of bleeds allowed, animals were not bled at time 0 right before HP administration. The values were normalized by subtracting the mean $\log_{10}$ (PFU/ml) found to be present in each group at time −10 min. Since the saline group shows no change in titer over the 120 min study, a change in titer during the 15 min interval between this point and the time of HP administration would not be expected. These values were 8.27±0.78, 8.75±0.1, 8.63±0.13, and 8.54±0.23 for saline, ΦX-CR1 HP (PEG), ΦX-CR1 HP (SMCC) and ΦX-PA HP (SMCC), respectively. The plots represent the means, and the bars the range, n=2.]

Having defined a useful dose of ΦX-CR1 HP (1 μg) to use in the transgenic mouse (FIG. 5), the kinetics of phage clearance in mice were then defined. Both CR1 transgenic and wt parental C57BL/6 mice were injected with $3\times10^7$ PFU of phage per mouse. ΦX-CR1 HP (SMCC) or control ΦX-PA HP (SMCC) were injected 45 minutes later. Blood was drawn from the mice 15 minutes prior to HP injection, and 15 minutes, 90 minutes, and 5 hours post HP injection. In control transgenic or wt mice that received a saline injection instead of HP, the phage titer in the circulation remained constant over 5 hours post injection. In CR1 transgenic mice the superiority of ΦX-CR1 HP over control ΦX-PA HP in reducing circulating phage was apparent within 15 minutes post infusion and continued out to 5 hours post infusion (FIG. 6*b*). The graph of FIG. 6*b*, like that of FIG. 6*a*, presents data that revealed HP-mediated clearance of phage in wild type versus CR-1 transgenic mice. [ΦX-CR1 HP (SMCC) was compared against ΦX-PA (SMCC) for its ability to clear injected bacteriophage ΦX174 from the bloodstream in CR1 transgenic and C57BL/6 wild type mice. Phage was injected iv at a dose of $3\times10^7$ PFU/mouse at time −45 minutes. The HPs or saline control were injected iv at time 0 at a dose of 1 μg/mouse. Blood was sampled at −15 minutes, 15 minutes, 90 minutes, and 5 hours post HP-injection by tail bleed. The graph represents the reduction in phage titer seen in blood at time post treatment. The values were normalized by subtracting the mean $\log_{10}$ (PFU/ml) found to be present in each group at time −15 minutes. Since the saline group shows no change in titer over the 5 hr study, a change in titer from −15 min to time 0 was not expected. These −15 minute values were 6.93±0.30, 7.45±0.08, 6.82±0.32, 7.35±0.11, and 6.96±0.40 for saline, CR1 mouse +ΦX-CR1 HP, CR1 mouse +ΦX-PA HP, wt mouse +ΦX-CR1 HP, and wt mouse +ΦX-PA HP, respectively. Error bars represent standard errors of the means, n=3. Asterisks indicate significant difference from the ΦX-PA HP at a $p<0.05$ by student's t-test.]

At all time points, ΦX-CR1 HP yielded approximately a 1.5 log greater reduction in circulating phage than control ΦX-PA HP. In wt mice lacking CR1 on E, ΦX-CR1 HP and control ΦX-PA, HP reduced the titer of circulating phage by similar levels at all time points and this reduction was similar to the level of reduction achieved by control ΦX-PA HP in the transgenic mouse.

These results demonstrated that an antibody HP that coupled phage to erythrocyte CR1 was more efficient than soluble phage-binding HP for removing phage from the serum and/or circulation in the transgenic mouse. The absence of this intravascular advantage in viral clearance in wt mice confirms the validity of the transgenic model.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A transgenic mouse whose genome comprises a polynucleotide encoding human complement receptor 1 (CR1) operably linked to a promoter, wherein the human CR1 molecule is expressed on the surface of erythrocytes of the transgenic mouse, and wherein the human CR1 binds immune complexes.

2. The transgenic mouse of claim 1, wherein the human CR1 molecule is preferentially expressed on the erythrocytes of the transgenic mouse.

3. The transgenic mouse of claim 1, wherein the promoter is a GATA-1 promoter.

4. The transgenic mouse of claim 1, wherein the promoter comprises the GATA-1 promoter and upstream regulatory elements thereof that increase CR1 expression on erythroid cells of the transgenic mouse.

5. The transgenic mouse of claim 1, wherein the transgenic mouse is homozygous for the polynucleotide.

6. The rodent of claim 1, wherein the transgenic mouse is heterozygous for the polynucleotide.

7. A method for screening for a bispecific compound capable of reducing the concentration of an agent in the serum and/or circulation of a subject, comprising:
  - administering a test bispecific compounds to the transgenic mouse of claim 4;
  - determining the ability of a bispecific compound to reduce the concentration of the agent in the serum and/or circulation of the transgenic mouse; and
  - selecting a bispecific compound that reduces the concentration of the agent in the serum and/or circulation of the transgenic mouse to thereby identify a bispecific compound capable of reducing the concentration of an agent in the serum and/or circulation of a subject.

8. A method for evaluating the ability of a bispecific compound to reduce the concentration of an agent in the serum and/or circulation of a subject comprising:
  - administering the bispecific compound to a transgenic mouse whose genome comprises a polynucleotide encoding human complement receptor 1 (CR1) operably linked to a promoter, wherein the human CR1 is functionally expressed on erythrocytes of the transgenic mouse; and
  - determining the ability of the bispecific compound to reduce the concentration of the agent in the serum and/or circulation of the transgenic mouse
  - to thereby evaluate the ability of the bispecific compound to reduce the concentration of the agent in the serum and/or circulation of the transgenic mouse.

9. The method of claim 7 or 8, further comprising administering the agent to the transgenic mouse.

10. The method of claim 9, wherein the agent is a pathogen.

11. The method of claim 9, wherein the agent is a virus.

12. The method of claim 9, wherein the agent is a toxin.

13. The method of claim 7 or 8, wherein the agent is a polynucleotide.

14. The method of claim 9, wherein the agent is a bacterium.

15. The method of claim 9, wherein the agent is an auto-antibody associated with an auto-immune disease.

16. The method of claim 7, or 8, wherein the bispecific compound is a bispecific compound that binds to human CR1.

17. The method of claim 16, wherein the bispecific compound is a heteropolymer.

18. The method of claim 16, wherein the bispecific compound is an antigen-based heteropolymer.

19. The method of claim 7 or 8, wherein the promoter is a GATA-1 promoter.

20. The method of claim 7 or 8, wherein the promoter comprises the GATA-1 promoter and an upstream control region activating expression on the erythrocytes of the transgenic mouse.

21. A method for making a transgenic mouse expressing human CR1 on the surface of its erythrocytes comprising:
  - a) introducing a polynucleotide encoding a human CR1 polypeptide into an egg or an embryo of a mouse, the polynucleotide operably linked to a promoter which causes human CR1 to be expressed on mouse erythrocytes; and
  - b) allowing the egg or embryo comprising the CR1 polynucleotide to develop to term to thereby produce a transgenic mouse transgenic mouse whose genome comprises a polynucleotide encoding a human CR1 polypeptide operably linked to a promoter, wherein the human CR1 polypeptide is expressed on the surface of erythrocytes of the transgenic mouse and binds immune complexes.

22. A method of producing a transgenic mouse, comprising breeding two transgenic mice, genomes of which comprise a polynucleotide encoding a human CR1 polypeptide operably liked to a promoter to thereby produce an offspring transgenic mouse whose genome comprises a polynucleotide encoding a human CR1 polypeptide operably linked to a promoter, wherein the human CR1 polypeptide is expressed on the surface erythrocytes of the transgenic mouse and binds immune complexes.

23. A method for screening for a bispecific compound capable of binding to human CR1 in the serum and/or circulation of a subject, comprising:
  - administering a test bispecific compounds to the transgenic mouse of claim 4;
  - determining the ability of a bispecific compound to bind human CR1 in the serum and/or circulation of the transgenic mouse; and
  - selecting a bispecific compound that binds human CR1 in the serum and/or circulation of the transgenic mouse to thereby identify a bispecific compound capable of binding human CR1 in the serum and/or circulation of a subject.

24. A method for evaluating the ability of a bispecific compound to bind human CR1 in the serum and/or circulation of a subject comprising:
  - administering the bispecific compound to a transgenic mouse whose genome comprises a polynucleotide encoding human complement receptor 1 (CR1) operably linked to a promoter, wherein the human CR1 is expressed on the surface of erythrocytes of the transgenic mouse; and
  - determining the ability of the bispecific compound to bind human CR1 in the serum and/or circulation of the transgenic mouse;
  - to thereby evaluate the ability of the bispecific compound to bind human CR1 in the serum and/or circulation of the transgenic mouse.

* * * * *